(12) United States Patent
Weitz et al.

(10) Patent No.: US 11,123,297 B2
(45) Date of Patent: *Sep. 21, 2021

(54) SYSTEMS AND METHODS FOR MAKING AND USING GEL MICROSPHERES

(71) Applicant: President and Fellows of Harvard College, Cambridge, MA (US)

(72) Inventors: David A. Weitz, Bolton, MA (US); Alireza Abbaspourrad, Ithaca, NY (US); Jing Fan, Cambridge, MA (US); Weixia Zhang, Arlington, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/768,135

(22) PCT Filed: Oct. 12, 2016

(86) PCT No.: PCT/US2016/056509
§ 371 (c)(1),
(2) Date: Apr. 13, 2018

(87) PCT Pub. No.: WO2017/066231
PCT Pub. Date: Apr. 20, 2017

(65) Prior Publication Data
US 2018/0296488 A1    Oct. 18, 2018

Related U.S. Application Data

(60) Provisional application No. 62/241,079, filed on Oct. 13, 2015.

(51) Int. Cl.
| | |
|---|---|
| *A61K 9/16* | (2006.01) |
| *B01J 13/00* | (2006.01) |
| *A61K 8/86* | (2006.01) |
| *A61K 8/87* | (2006.01) |
| *A61Q 19/00* | (2006.01) |
| *A61K 8/04* | (2006.01) |
| *A61K 47/60* | (2017.01) |
| *A61K 47/69* | (2017.01) |
| *A61K 9/50* | (2006.01) |
| *A61K 47/54* | (2017.01) |
| *B01J 13/14* | (2006.01) |

(Continued)

(52) U.S. Cl.
CPC ........... *A61K 9/1682* (2013.01); *A61K 8/044* (2013.01); *A61K 8/86* (2013.01); *A61K 8/87* (2013.01); *A61K 9/1635* (2013.01); *A61K 9/5026* (2013.01); *A61K 9/5089* (2013.01); *A61K 47/549* (2017.08); *A61K 47/60* (2017.08); *A61K 47/6903* (2017.08); *A61K 47/6921* (2017.08); *A61Q 19/00* (2013.01); *B01J 13/0065* (2013.01); *B01J 13/0069* (2013.01); *B01J 13/14* (2013.01); *B01J 13/20* (2013.01); *A61K 9/113* (2013.01); *A61K 2800/10* (2013.01); *A61K 2800/412* (2013.01); *A61K 2800/81* (2013.01); *A61K 2800/95* (2013.01); *B01J 2219/00177* (2013.01)

(58) Field of Classification Search
CPC ......... A61K 9/1682; A61K 8/86; A61K 8/87; A61K 8/044; A61K 47/60; A61K 47/6903; A61K 9/5026; A61K 9/5089; A61K 47/549; A61K 47/6921; A61K 9/1635; A61K 9/113; A61K 2800/95; A61K 2800/10; A61K 2800/81; A61K 2800/412; B01J 13/0065; B01J 13/0069; B01J 13/14; B01J 13/20; B01J 2219/0017; A61Q 19/00

See application file for complete search history.

(56) References Cited

U.S. PATENT DOCUMENTS

| | | |
|---|---|---|
| 4,732,930 A | 3/1988 | Tanaka et al. |
| 4,743,507 A | 5/1988 | Franses et al. |
| 4,996,265 A | 2/1991 | Okubo et al. |

(Continued)

FOREIGN PATENT DOCUMENTS

| | | |
|---|---|---|
| CN | 1150764 A | 5/1997 |
| EP | 0 249 007 A2 | 12/1987 |
| EP | 0 272 659 A2 | 6/1988 |
| EP | 0 478 326 A1 | 4/1992 |
| EP | 1 019 496 B1 | 9/2004 |
| EP | 1 482 036 B1 | 10/2007 |
| EP | 1 594 980 B1 | 11/2009 |

(Continued)

OTHER PUBLICATIONS

Invitation to Pay Additional Fees for PCT Application PCT/US09/005184 dated May 27, 2010.

(Continued)

*Primary Examiner* — Shirley V Gembeh
(74) *Attorney, Agent, or Firm* — Wolf, Greenfield & Sacks, P.C.

(57) ABSTRACT

The present invention generally relates to microfluidic droplets and, in particular, to multiple emulsion microfluidic droplets. In certain aspects, particles such as gel particles can be prepared in an aqueous carrier from aqueous droplets (or a non-aqueous carrier from non-aqueous droplets). For example, in some embodiments, double-emulsion droplets of a first fluid, surrounded by a second fluid, contained in a carrier fluid may be prepared, where the first fluid forms a gel and the second fluid is removed. For instance, the second fluid may be dissolved in the carrier fluid, or the second fluid may be hardened, then removed, for example, due to a change in pH. Other embodiments of the present invention are generally directed to kits containing such microfluidic droplets, microfluidic devices for making such microfluidic droplets, or the like.

18 Claims, 6 Drawing Sheets

(51) Int. Cl.
*B01J 13/20* (2006.01)
*A61K 9/113* (2006.01)

(56) References Cited

U.S. PATENT DOCUMENTS

| | | | |
|---|---|---|---|
| 5,055,390 A | 10/1991 | Weaver et al. | |
| 5,100,933 A | 3/1992 | Tanaka et al. | |
| 5,120,349 A | 6/1992 | Stewart et al. | |
| 5,149,625 A | 9/1992 | Church et al. | |
| 5,202,231 A | 4/1993 | Drmanac et al. | |
| 5,216,096 A | 6/1993 | Hattori et al. | |
| 5,326,692 A | 7/1994 | Brinkley et al. | |
| 5,436,130 A | 7/1995 | Mathies et al. | |
| 5,500,223 A | 3/1996 | Behan et al. | |
| 5,512,131 A | 4/1996 | Kumar et al. | |
| 5,695,940 A | 12/1997 | Drmanac et al. | |
| 5,736,330 A | 4/1998 | Fulton | |
| 5,834,252 A | 11/1998 | Stemmer et al. | |
| 5,849,055 A | 12/1998 | Arai et al. | |
| 5,851,769 A | 12/1998 | Gray et al. | |
| 6,046,003 A | 4/2000 | Mandecki | |
| 6,051,377 A | 4/2000 | Mandecki | |
| 6,057,107 A | 5/2000 | Fulton | |
| 6,103,537 A | 8/2000 | Ullman et al. | |
| 6,297,006 B1 | 10/2001 | Drmanac et al. | |
| 6,297,017 B1 | 10/2001 | Schmidt et al. | |
| 6,355,198 B1 | 3/2002 | Kim et al. | |
| 6,361,950 B1 | 3/2002 | Mandecki | |
| 6,380,297 B1 | 4/2002 | Zion et al. | |
| 6,432,360 B1 | 8/2002 | Church | |
| 6,485,944 B1 | 11/2002 | Church et al. | |
| 6,500,447 B1 | 12/2002 | Dexter et al. | |
| 6,511,803 B1 | 1/2003 | Church et al. | |
| 6,524,456 B1 | 2/2003 | Ramsey et al. | |
| 6,586,176 B1 | 7/2003 | Trnovsky et al. | |
| 6,632,606 B1 | 10/2003 | Ullman et al. | |
| 6,670,133 B2 | 12/2003 | Knapp et al. | |
| 6,767,731 B2 | 7/2004 | Hannah | |
| 6,800,298 B1 | 10/2004 | Burdick et al. | |
| 6,806,058 B2 | 10/2004 | Jesperson et al. | |
| 6,913,935 B1 | 7/2005 | Thomas | |
| 6,929,859 B2 | 8/2005 | Chandler et al. | |
| 7,041,481 B2 | 5/2006 | Anderson et al. | |
| 7,268,167 B2 | 9/2007 | Higuchi et al. | |
| 7,425,431 B2 | 9/2008 | Church et al. | |
| 7,536,928 B2 | 5/2009 | Kazuno | |
| 7,604,938 B2 | 10/2009 | Takahashi et al. | |
| 7,638,276 B2 | 12/2009 | Griffiths et al. | |
| 7,708,949 B2 | 5/2010 | Stone et al. | |
| 7,776,927 B2 | 8/2010 | Chu et al. | |
| RE41,780 E | 9/2010 | Anderson et al. | |
| 7,799,553 B2 | 9/2010 | Mathies et al. | |
| 7,968,287 B2 | 6/2011 | Griffiths et al. | |
| 8,252,539 B2 | 8/2012 | Quake et al. | |
| 8,273,573 B2 | 9/2012 | Ismagilov et al. | |
| 8,278,071 B2 | 10/2012 | Brown et al. | |
| 8,329,407 B2 | 12/2012 | Ismagilov et al. | |
| 8,748,094 B2 | 6/2014 | Weitz et al. | |
| 8,748,102 B2 | 6/2014 | Berka et al. | |
| 8,765,380 B2 | 7/2014 | Berka et al. | |
| 8,871,444 B2 | 10/2014 | Griffiths et al. | |
| 9,017,948 B2 | 4/2015 | Agresti et al. | |
| 9,029,085 B2 | 5/2015 | Agresti et al. | |
| 9,039,273 B2 | 5/2015 | Weitz et al. | |
| 9,068,210 B2 | 6/2015 | Agresti et al. | |
| 9,689,024 B2 | 6/2017 | Hindson et al. | |
| 9,816,121 B2 | 6/2017 | Agresti et al. | |
| 9,695,468 B2 | 7/2017 | Hindson et al. | |
| 9,718,044 B2 | 8/2017 | Wesner et al. | |
| 9,850,526 B2 | 12/2017 | Agresti et al. | |
| 9,856,530 B2 | 1/2018 | Hindson et al. | |
| 10,221,437 B2 | 3/2019 | Weitz et al. | |
| 10,471,016 B2 | 11/2019 | Weitz et al. | |
| 10,508,294 B2 | 12/2019 | Weitz et al. | |
| 10,683,524 B2 | 6/2020 | Weitz et al. | |
| 10,738,337 B2 | 8/2020 | Weitz et al. | |
| 10,941,430 B2 | 3/2021 | Weitz et al. | |
| 2001/0020588 A1 | 9/2001 | Adourian et al. | |
| 2001/0044109 A1 | 11/2001 | Mandecki | |
| 2002/0034737 A1 | 3/2002 | Drmanac | |
| 2002/0034747 A1 | 3/2002 | Bruchez et al. | |
| 2002/0051992 A1 | 5/2002 | Bridgham et al. | |
| 2002/0092767 A1 | 7/2002 | Bjornson et al. | |
| 2002/0179849 A1 | 12/2002 | Maher et al. | |
| 2003/0008285 A1 | 1/2003 | Fischer | |
| 2003/0008323 A1 | 1/2003 | Ravkin et al. | |
| 2003/0028981 A1 | 2/2003 | Chandler et al. | |
| 2003/0039978 A1 | 2/2003 | Hannah | |
| 2003/0044777 A1 | 3/2003 | Beattie | |
| 2003/0044836 A1 | 3/2003 | Levine et al. | |
| 2003/0099954 A1 | 5/2003 | Miltenyi et al. | |
| 2003/0104466 A1 | 6/2003 | Knapp et al. | |
| 2003/0108897 A1 | 6/2003 | Drmanac | |
| 2003/0170698 A1 | 9/2003 | Gascoyne et al. | |
| 2003/0182068 A1 | 9/2003 | Battersby et al. | |
| 2003/0207260 A1 | 11/2003 | Trnovsky et al. | |
| 2003/0215862 A1 | 11/2003 | Parce et al. | |
| 2004/0063138 A1 | 4/2004 | McGinnis et al. | |
| 2004/0096515 A1 | 5/2004 | Bausch et al. | |
| 2004/0132122 A1 | 7/2004 | Banerjee et al. | |
| 2004/0253613 A1 | 12/2004 | Taylor et al. | |
| 2005/0019839 A1 | 1/2005 | Jesperson et al. | |
| 2005/0042625 A1 | 2/2005 | Schmidt et al. | |
| 2005/0123614 A1 | 6/2005 | Kim et al. | |
| 2005/0136486 A1 | 6/2005 | Haushalter | |
| 2005/0172476 A1 | 8/2005 | Stone et al. | |
| 2005/0181379 A1 | 8/2005 | Su et al. | |
| 2005/0202429 A1 | 9/2005 | Trau et al. | |
| 2005/0221339 A1 | 10/2005 | Griffiths et al. | |
| 2005/0244850 A1 | 11/2005 | Huang et al. | |
| 2005/0287572 A1 | 12/2005 | Mathies et al. | |
| 2006/0020371 A1 | 1/2006 | Ham et al. | |
| 2006/0073487 A1 | 4/2006 | Oliver et al. | |
| 2006/0078888 A1 | 4/2006 | Griffiths et al. | |
| 2006/0078893 A1 | 4/2006 | Griffiths et al. | |
| 2006/0153924 A1 | 7/2006 | Griffiths et al. | |
| 2006/0163385 A1 | 7/2006 | Link et al. | |
| 2006/0240506 A1 | 10/2006 | Kushmaro et al. | |
| 2006/0257893 A1 | 11/2006 | Takahashi et al. | |
| 2006/0292583 A1 | 12/2006 | Schneider et al. | |
| 2007/0003442 A1 | 1/2007 | Link et al. | |
| 2007/0020617 A1 | 1/2007 | Trnovsky et al. | |
| 2007/0054119 A1 | 3/2007 | Garstecki et al. | |
| 2007/0092914 A1 | 4/2007 | Griffiths et al. | |
| 2007/0172827 A1 | 7/2007 | Murakami | |
| 2007/0172873 A1 | 7/2007 | Brenner et al. | |
| 2007/0195127 A1 | 8/2007 | Ahn et al. | |
| 2007/0228588 A1 | 10/2007 | Noritomi et al. | |
| 2007/0264320 A1 | 11/2007 | Lee et al. | |
| 2008/0003142 A1 | 1/2008 | Link et al. | |
| 2008/0004436 A1 | 1/2008 | Tawfik et al. | |
| 2008/0014589 A1 | 1/2008 | Link et al. | |
| 2009/0012187 A1 | 1/2009 | Chu et al. | |
| 2009/0035770 A1 | 2/2009 | Mathies et al. | |
| 2009/0068170 A1 | 3/2009 | Weitz et al. | |
| 2009/0131543 A1 | 5/2009 | Weitz et al. | |
| 2009/0134027 A1 | 5/2009 | Jary | |
| 2009/0191276 A1 | 7/2009 | Kim et al. | |
| 2009/0197772 A1 | 8/2009 | Griffiths et al. | |
| 2009/0286687 A1 | 11/2009 | Dressman et al. | |
| 2010/0022414 A1 | 1/2010 | Link et al. | |
| 2010/0130369 A1 | 5/2010 | Shenderov et al. | |
| 2010/0136544 A1 | 6/2010 | Agresti et al. | |
| 2010/0137163 A1 | 6/2010 | Link et al. | |
| 2010/0173394 A1 | 7/2010 | Colston, Jr. et al. | |
| 2010/0210479 A1 | 8/2010 | Griffiths et al. | |
| 2010/0213628 A1 | 8/2010 | Bausch et al. | |
| 2010/0273219 A1 | 10/2010 | May et al. | |
| 2011/0033854 A1 | 2/2011 | Drmanac et al. | |
| 2011/0086780 A1 | 4/2011 | Colston et al. | |
| 2011/0092392 A1 | 4/2011 | Colston et al. | |
| 2011/0160078 A1 | 6/2011 | Fodor et al. | |
| 2011/0218123 A1 | 9/2011 | Weitz et al. | |
| 2011/0229545 A1 | 9/2011 | Shum et al. | |

(56) References Cited

U.S. PATENT DOCUMENTS

| | | |
|---|---|---|
| 2011/0267457 A1 | 11/2011 | Weitz et al. |
| 2011/0305761 A1 | 12/2011 | Shum et al. |
| 2012/0003321 A1 | 1/2012 | Peng et al. |
| 2012/0010107 A1 | 1/2012 | Griffiths et al. |
| 2012/0015382 A1 | 1/2012 | Weitz et al. |
| 2012/0015822 A1 | 1/2012 | Weitz et al. |
| 2012/0076860 A1 | 3/2012 | Trout et al. |
| 2012/0135407 A1 | 5/2012 | Slatter |
| 2012/0190032 A1 | 7/2012 | Ness et al. |
| 2012/0199226 A1 | 8/2012 | Weitz et al. |
| 2012/0211084 A1 | 8/2012 | Weitz et al. |
| 2012/0220494 A1 | 8/2012 | Samuels et al. |
| 2012/0220497 A1 | 8/2012 | Jacobson et al. |
| 2012/0222748 A1 | 9/2012 | Weitz et al. |
| 2013/0004522 A1 | 1/2013 | Taylor et al. |
| 2013/0046030 A1 | 2/2013 | Rotem et al. |
| 2013/0064862 A1 | 3/2013 | Weitz et al. |
| 2013/0079231 A1 | 3/2013 | Pushkarev et al. |
| 2013/0109575 A1 | 5/2013 | Kleinschmidt et al. |
| 2013/0157899 A1 | 6/2013 | Adler et al. |
| 2013/0210639 A1 | 8/2013 | Link et al. |
| 2013/0274117 A1 | 10/2013 | Church et al. |
| 2014/0065234 A1 | 3/2014 | Shum et al. |
| 2014/0155295 A1 | 6/2014 | Hindson et al. |
| 2014/0199730 A1 | 7/2014 | Agresti et al. |
| 2014/0199731 A1 | 7/2014 | Agresti et al. |
| 2014/0220350 A1 | 8/2014 | Kim et al. |
| 2014/0227684 A1 | 8/2014 | Hindson et al. |
| 2014/0235506 A1 | 8/2014 | Hindson et al. |
| 2014/0303039 A1 | 10/2014 | Weitz et al. |
| 2014/0378349 A1 | 12/2014 | Hindson et al. |
| 2015/0005200 A1 | 1/2015 | Hindson et al. |
| 2015/0314292 A1 | 11/2015 | Weitz et al. |
| 2015/0336068 A1 | 11/2015 | Weitz et al. |
| 2015/0336069 A1 | 11/2015 | Weitz et al. |
| 2015/0336070 A1 | 11/2015 | Weitz et al. |
| 2015/0336071 A1 | 11/2015 | Weitz et al. |
| 2015/0336072 A1 | 11/2015 | Weitz et al. |
| 2015/0337371 A1 | 11/2015 | Weitz et al. |
| 2015/0353999 A1 | 12/2015 | Agresti et al. |
| 2016/0279068 A1 | 9/2016 | Utech et al. |
| 2017/0183701 A1 | 6/2017 | Agresti et al. |
| 2017/0224849 A1 | 8/2017 | Carroll et al. |
| 2017/0319443 A1 | 12/2017 | Weitz et al. |
| 2018/0023109 A1 | 1/2018 | Weitz et al. |
| 2018/0119212 A1 | 5/2018 | Weitz et al. |
| 2018/0171373 A1 | 6/2018 | Weitz et al. |
| 2018/0214385 A1 | 8/2018 | Weitz et al. |
| 2020/0000274 A1 | 1/2020 | Weitz et al. |
| 2020/0085753 A1 | 3/2020 | Weitz et al. |
| 2020/0157593 A1 | 5/2020 | Weitz et al. |
| 2020/0197894 A1 | 6/2020 | Weitz et al. |

FOREIGN PATENT DOCUMENTS

| | | |
|---|---|---|
| EP | 1 967 592 B1 | 4/2010 |
| EP | 2 258 846 A2 | 12/2010 |
| EP | 2 145 955 B1 | 2/2012 |
| EP | 1 905 828 B1 | 8/2012 |
| EP | 1 908 832 B1 | 12/2012 |
| EP | 2 540 389 A1 | 1/2013 |
| JP | S59-049832 A2 | 3/1984 |
| JP | 2004-361291 A | 12/2004 |
| JP | 2006-507921 T2 | 3/2006 |
| JP | 2006-289250 A | 10/2006 |
| JP | 2007-268350 A | 10/2007 |
| JP | 2007-298327 A | 11/2007 |
| JP | 2008-535644 A | 9/2008 |
| JP | 2009-208074 A2 | 9/2009 |
| JP | 2014-522718 A | 9/2014 |
| KR | 2014/0107381 A | 9/2014 |
| WO | WO 95/09613 A1 | 4/1995 |
| WO | WO 1996/29629 A2 | 9/1996 |
| WO | WO 1996/41011 A1 | 12/1996 |
| WO | WO 1999/09217 A1 | 2/1999 |
| WO | WO 1999/52708 A1 | 10/1999 |
| WO | WO 2000/08212 A1 | 2/2000 |
| WO | WO 2000/26412 A1 | 5/2000 |
| WO | WO 2001/14589 A2 | 3/2001 |
| WO | WO 2001/89787 A2 | 5/2001 |
| WO | WO 2002/31203 A2 | 10/2001 |
| WO | WO 2001/85138 A2 | 11/2001 |
| WO | WO 2002/047665 A2 | 6/2002 |
| WO | WO 2002/86148 A1 | 10/2002 |
| WO | WO 03/028653 A2 | 4/2003 |
| WO | WO 2004/002627 A2 | 6/2003 |
| WO | WO 2004/091763 A2 | 4/2004 |
| WO | WO 2005/021151 A1 | 8/2004 |
| WO | WO 2005/040406 A1 | 10/2004 |
| WO | WO 2004/102204 A1 | 11/2004 |
| WO | WO 2004/103565 A2 | 12/2004 |
| WO | WO 2004/105734 A1 | 12/2004 |
| WO | WO 2005/082098 A2 | 2/2005 |
| WO | WO 2005/041884 A2 | 5/2005 |
| WO | WO 2005/049787 A2 | 6/2005 |
| WO | WO 2005/084210 A2 | 9/2005 |
| WO | WO 2005/103106 A1 | 11/2005 |
| WO | WO 2006/078841 A1 | 1/2006 |
| WO | WO 2006/096571 A2 | 3/2006 |
| WO | WO 2007/081387 A1 | 6/2006 |
| WO | WO 2006/096571 * | 9/2006 |
| WO | WO 2007/001448 A2 | 1/2007 |
| WO | WO 2007/002490 A2 | 1/2007 |
| WO | WO 2007/012638 A1 | 2/2007 |
| WO | WO 2007/024840 A2 | 3/2007 |
| WO | WO 2007/081385 A2 | 7/2007 |
| WO | WO 2007/089541 A2 | 8/2007 |
| WO | WO 2008/021123 A1 | 8/2007 |
| WO | WO 2007/114794 A1 | 10/2007 |
| WO | WO 2007/121489 A2 | 10/2007 |
| WO | WO 2007/133710 A2 | 11/2007 |
| WO | WO 2007/133807 A2 | 11/2007 |
| WO | WO 2007/138178 A2 | 12/2007 |
| WO | WO 2007/139766 A2 | 12/2007 |
| WO | WO 2007/140015 A2 | 12/2007 |
| WO | WO 2007/149432 A2 | 12/2007 |
| WO | WO 2008/091792 A2 | 1/2008 |
| WO | WO 2008/058297 A2 | 5/2008 |
| WO | WO 2009/005680 A1 | 6/2008 |
| WO | WO 2009/011808 A1 | 7/2008 |
| WO | WO 2008/102057 A1 | 8/2008 |
| WO | WO 2008/109176 A2 | 9/2008 |
| WO | WO 2008/121342 A2 | 10/2008 |
| WO | WO 2008/134153 A1 | 11/2008 |
| WO | WO 2009/085215 A1 | 12/2008 |
| WO | WO 2009/120254 A1 | 10/2009 |
| WO | WO 2009/148598 A1 | 12/2009 |
| WO | WO 2010/104604 A1 | 9/2010 |
| WO | WO 2010/151776 A2 | 12/2010 |
| WO | WO 2011/028760 A2 | 3/2011 |
| WO | WO 2011/028764 A2 | 3/2011 |
| WO | WO 2011/056546 A1 | 5/2011 |
| WO | WO 2011/116154 A2 | 9/2011 |
| WO | WO 2012/048341 A1 | 4/2012 |
| WO | WO 2012/156744 A2 | 11/2012 |
| WO | WO 2012/162296 A2 | 11/2012 |
| WO | WO 2013/006661 A2 | 1/2013 |
| WO | WO 2013/032709 A2 | 3/2013 |
| WO | WO 2013/083760 A2 | 6/2013 |
| WO | WO 2013/177220 A2 | 11/2013 |
| WO | WO 2015/069634 A1 | 5/2015 |
| WO | WO 2015/160919 A1 | 10/2015 |
| WO | WO 2016/085739 | 6/2016 |
| WO | WO 2017/066231 | 4/2017 |

OTHER PUBLICATIONS

International Search Report and Written Opinion of the International Searching Authority for International Application No. PCT/US2009/005184, dated Aug. 16, 2010.
International Preliminary Report on Patentability for PCT Application PCT/US09/005184 dated Mar. 31, 2011.

(56) References Cited

OTHER PUBLICATIONS

International Search Report and Written Opinion dated Jan. 10, 2017 for Application No. PCT/US2016/056509.
International Preliminary Report on Patentability from PCT Application PCT/US2016/056509 dated Apr. 26, 2018.
Extended European Search Report for Application No. EP 14860623.9 dated May 23, 2017.
International Search Report and Written Opinion from PCT Application PCT/US2014/063846 dated Mar. 10, 2015.
Invitation to Pay Additional Fees from PCT Application PCT/US2014/063846 dated Jul. 1, 2015.
International Preliminary Report on Patentability from PCT Application PCT/US2014/063846 dated May 19, 2016.
[No Author Listed], Toxnet, Toxicology Data Network. Vinyl Toluene. National Library of Medicine. 2015:1-38.
[No Author] Gene Characterization Kits. Stratagene Catalog. Statagene Cloning Systems: Tools and Technology for Lift Sciences. 1988. 3 pages.
[No Author] Microfluidic ChipShop. Microfluidic product catalogue. Mar. 2005.
[No Author] Microfluidic ChipShop. Microfluidic product catalogue. Oct. 2009.
Abate et al., Droplet Based Sequencing. Americal Physical Society. Presentation. Mar. 12, 2008. 25 Pages.
Abate et al., Valve-based flow focusing for drog formation. Appl Phys Lett. 2009;94. 3 pages.
Adams et al., Entropically driven microphase transitions in mixtures of colloidal rods and spheres. Nature. May 28, 1998:393:349-52.
Agresti, "Selection of ribozymes that catalyse multiple-turnover Diels-Alder cycloadditions by using in vitro compartmentalization," PNAS, 102, 16170-16175 (2005).
Akselband, "Enrichment of slow-growing marine microorganisms from mixed cultures using gel microdrop (GMD) growth assay and fluorescence-activated cell sorting," J. Exp. Marine Biol., 329: 196-205 (2006).
Akselband, "Rapid mycobacteria drug susceptibility testing using gel microdrop (GMD) growth assay and flow cytometry," J. Microbiol. Methods, 62:181-197 (2005).
Anna et al., "Formation of dispersions using 'flow focusing' in microchannels," Appin. Phys. Letts. 82:3 364 (2003).
Baret et al., Fluorescence-activated droplet sorting (FADS): efficient microfluidic cell sorting based on enzymatic activity. Lab Chip. Jul. 7, 2009;9(13):1850-8. doi: 10.1039/b902504a. Epub Apr. 23, 2009.
Boone, et al. Plastic advances microfluidic devices. The devices debuted in silicon and glass, but plastic fabrication may make them hugely successful in biotechnology application. Analytical Chemistry. Feb. 2002; 78A-86A.
Braeckmans et al., Scanning the Code. Modern Drug Discovery. 2003:28-32.
Carroll, The selection of high-producing cell lines using flow cytometry and cell sorting. Exp Op Biol Therp. 2004;4(11):1821-1829.
Chaudhary, "A rapid method of cloning functional variable-region antibody genes in *Escherichia coli* as single-chain immunotoxins," PNAS, 87, 1066-1070 (Feb. 1990).
Chechetkin et al., Sequencing by hybridization with the generic 6-mer oligonucleotide microarray: an advanced scheme for data processing. J Biomol Struct Dyn. Aug. 2000;18(1):83-101.
Chou, et al. Disposable Microdevices for DNA Analysis and Cell Sorting. Proc. Solid-State Sensor and Actuator Workshop, Hilton Head, Sc. Jun. 8-11, 1998; 11-14.
Chu, et al., "Controllable Monodisperse Multiple Emulsions," Ang. Chem. Int. Ed., 46:8970-8974 (2007).
Clausell-Tormos et al., "Droplet-based microfluidic platforms for the encapsulation and screening of mammalian cells and multicellular organisms," Chem. Biol. 15:427-437 (2008).
De Bruin et al., UBS Investment Research. Q-Series®: DNA Sequencing. UBS Securities LLC. Jul. 12, 2007. 15 pages.
Dendukuri et al. Continuous-flow lithography for high-throughput microparticle synthesis. Nature Mat. May 2006;5:365-69.

Diaz R.V. et al., "One-month sustained release microspheres of 125I-bovine calcitonin In vitro—in vivo studies," J. Controlled Release, 59:55-26 (1999).
Doerr, "The smallest bioreactor," Nature Methods, 2:5, 326 (2005).
Draget et al., Alginate based new materials. Int J Biol Macromol. Aug. 1997;21(1-2):47-55.
Drmanac eta l., Sequencing by hybridization (SBH): advantages, achievements, and opportunities. Adv Biochem Eng Biotechnol. 2002;77:75-101.
Durant et al., Effects of cross-linking on the morphology of structured latex particles 1. Theoretical considerations. Macromol. 1996;29:8466-72. Month not cited on publication.
Fu, "A microfabricated fluorescence-activated cell sorter," Nature Biotech., 17:1109-1111 (1997).
Fulton et al., Advanced multiplexed analysis with the FlowMetrix system. Clin Chem. Sep. 1997;43(9):1749-56.
Gartner, et al. The Microfluidic Toolbox—examples for fluidic interfaces and standardization concepts. Proc. SPIE 4982, Microfluidics, BioMEMS, and Medical Microsystems, (Jan. 17, 2003); doi: 10.1117/12.479566.
Ghadessy et al. Directed evolution of polymerase function by compartmentalized self-replication. Proc Natl Acad Sci USA. Apr. 10, 2001; 98(8):4552-7. Epub Mar. 27, 2001.
Gordon et al., Self-assembled polymer membrane capsules inflated by osmotic pressure. JACS. 2004;126:14117-22. Published on web Oct. 12, 2004.
Graham et al., Nanogels and microgels: The new polymeric materials playground. Pure Appl Chem. 1998;70(6):1271-75. Month not cited on publication.
He, M. "Selective Encapsulation of Single Cells and Subcellular Organelles into Picoliter- and Femtoliter—vol. Droplets," Anal. Chem., 77:1539-1544 (2005).
Holtze et al., Biocompatible surfactants for water-in-fluorocarbon emulsions. Lab Chip. Oct. 2008; 8(10):1632-9.
Hsu et al., Self-assembled shells composed of colloidal particles: fabrication and characterization. Langmuir. 2005;21:2963-70. Published on web Feb. 23, 2005.
Huebner, "Quantitative detection of protein expression in single cells using droplet microfluidics," A. Chem. Commun. 1218-1220 (2007).
Hug et al. Measurement of the number of molecules of a single mRNA species in a complex mRNA preparation. J Theor Biol. Apr. 21, 2003; 221(4):615-24.
Jogun et al., Rheology and microstructure of dense suspensions of plate-shaped colloidal particles. J. Rheol. Jul./Aug. 1999;43:847-71.
Khatiwala et al., "Intrinsic mechanical properties of the extracellular matrix affect the behaviour of pre-osteoblastic MC3T3-E1 cells" Am. J. Physiol. Cell Physiol. 2006;290:C1640.
Khetani et al., Microscale culture of human liver cells for drug development. Nat Biotechnol. Jan. 2008;26(1):120-6. Epub Nov. 18, 2007.
Khomiakova et al., [Analysis of perfect and mismatched DNA duplexes by a generic hexanucleotide microchip]. Mol Biol (Mosk). Jul.-Aug. 2003;37(4):726-41. Russian. Abstract.
Kim et al., Colloidal assembly route for responsive colloidsomes with tunable permeability. Nano Lett. 2007;7:2876-80. Published on web Aug. 3, 2007.
Kim et al., Fabrication of monodisperse gel shells and functional microgels in microfluidic devices. Angew Chem Int Ed. 2007;46:1819-22. Month not cited on publication.
Kim et al., Monodisperse nonspherical colloid materials with well-defined structures. Presentation. Sep. 16, 2005. 5 pages.
Kim et al., Synthesis of nonspherical colloidal particles with anisotropic properties. JACS. 2006;128:14374-77. Published on web Oct. 18, 2006.
Kim et al., Uniform nonspherical colloidal particles engineered by geometrically tunable gradient of crosslink density. 80th ACS Colloid Surf. Sci. Symp. Jun. 20, 2006. 23 pages.
Kim et al., Uniform nonspherical colloidal particles with tunable shapes. Adv. Mater. 2007;19:2005-09. Month not cited on publication.

(56) References Cited

OTHER PUBLICATIONS

Kim, J-H, "Albumin loaded microsphere of amphiphilic poly(ethylene glycol)/poly(α-ester) multiblock copolymer," Eu. J. Pharm. Sciences, 23:245-251 (2004).
Kim, J-W, "Fabrication of monodisperse gel shells and functional microgels in microfluidic devices," Angew. Chem., 119:1851-1854 (2007).
Klein et al., Cell-cycle control by physiological matrix elasticity and in vivo tissue stiffening. Curr Biol. Sep. 29, 2009;19(18):1511-8. doi: 10.1016/j.cub.2009.07.069. Epub Sep. 17, 2009.
Koo et al., A snowman-like array of colloidal dimers for antireflecting surfaces. Adv Mater. Feb. 3, 2004;16(3):274-77.
Koster et al., "Drop-based microfluidic devices for encapsulation of single cells," Lab on a Chip the Royal Soc. of Chem. 8:1110-1115 (2008).
Kumar et al., Biodegradable block copolymers. Adv Drug Deliv Rev. Dec. 3, 2001;53(1):23-44.
Kumaresan et al. High-Throughput Single Copy DNA Amplification and Cell Analysis in Engineered Nanoliter Droplets. Anal Chem. 2008. 80:3522-3529.
Landfester et al. Preparation of Polymer Particles in Nonaqueous Direct and Inverse Miniemulsions. Macromolecules. Mar. 11, 2000;33(7):2370-2376.
Landfester et al., Formulation and Stability Mechanisms of Polymerizable Miniemulsions. Macromolecules. 1999;32:5222-5228. Published on web Jul. 22, 1999.
Lee et al., Double emulsion-templated nanoparticle colloidosomes with selective permeability. Adv Mater. 2008;20:3498-503. Month not cited on publication.
Li, Y., et al. "PEGylated PLGA nanoparticles as protein carriers: synthesis, preparation and biodistribution in rats," J. of Controlled Release, vol. 71, pp. 203-211 (2001).
Lin et al., Ultrathin cross-linked nanoparticle membranes. JACS. 2003;125:12690-91. Published on web Sep. 27, 2003.
Lorenceau et al., Generation of polymerosomes from double-emulsions. Langmuir. Sep. 27, 2005;21(20):9183-6.
Loscertales, "Micro/Nano encapsulation via electrified coaxial liquid jets," Science 295:1695 (2002).
Love, "A microengraving method for rapid selection of single cells producing antigen-specific antibodies," Nature Biotech, 24:6, 703 (Jun. 2006).
Manoharan et al., Dense packing and symmetry in small clusters of microspheres. Science. Jul. 25, 2003;301:483-87.
Mazutis et al., Selective droplet coalescence using microfluidic systems. Lab Chip. Apr. 24, 2012; 12(10):1800-6.
Mirzabekov, "DNA sequencing by hybridization—a megasequencing method and diagnostic tool?" T/B Tech, 12:27-32 (1994).
Mock et al., Synthesis of anisotropic nanoparticles by seeded emulsion polymerization. Langmuir. Apr. 25, 2006;22(9):4037-43. Published on web Mar. 31, 2006.
Mouritzen et al., Single nucleotide polymorphism genotyping using locked nucleic acid (LNA). Expert Rev Mol Diagn. Jan. 2003;3(1):27-38.
Nguyen, "In situ hybridization to chromosomes stabilized in gel microdrops," Cytometry, 21:111-119 (1995).
Nikolaides et al., Two Dimensional Crystallisation on Curved Surfaces. MRS Fall 2000 Meeting. Boston, MA. Nov. 27, 2000. Abstract #41061.
Okubo et al., Micron-sized, monodisperse, snowman/confetti-shaped polymer particles by seeded dispersion polymerization. Colloid Polym. Sci. 2005;283:1041-45. Published online Apr. 2, 2005.
Okushima, "Controlled production of monodisperse double emulsions by two-step droplet breakup in microfluidic devices," Langmuir, 20:9905-9908 (2004).
Park et al., Shear-reversibly crosslinked alginate hydrogels for tissue engineering. Macromol Biosci. Sep. 9, 2009;9(9):895-901. doi: 10.1002/mabi.200800376.

Perez, C. et al., "Poly(lactic acid)-poly(ethylene glycol) nanoparticles as new carriers for the delivery of plasmid DNA," J. Controlled Release, vol. 75, pp. 211-224 (2001).
Reculusa et al., Synthesis of daisy-shaped and multipod-like silica/polystyrene nanocomposites. Nano Lett. 2004;4:1677-82. Published on web Jul. 14, 2004.
Rimann et al., Synthetic 3D multicellular systems for drug development. Curr Opin Biotechnol. Oct. 2012;23(5):803-9. doi:10.1016/j.copbio.2012.01.011. Epub Feb. 10, 2012.
Roh et al., Biphasic janus particles with nanoscale anisotropy. Nature Med. Oct. 2005;4:759-63.
Ryan, "Rapid assay for mycobacterial growth and antibiotic susceptibility using gel microdrop and encapsulation," J. Clinical Microbiol., 33:1720-1726 (1995).
Sakai et al., Both ionically and enzymatically crosslinkable alginate-tyramine conjugate as materials for cell encapsulation. J Biomed Mater Res A. May 2008;85(2):345-51.
Schirinzi et al., Combinatorial sequencing-by-hybridization: analysis of the NF1 gene. Genet Test. 2006 Spring;10(1):8-17.
Schmitt, "Bead-based multiplex genotyping of human papillomaviruses," J. Clinical Microbiol., 44:2 504-512 (2006).
Schmitz et al., Dropspots: a picoliter array in a microfluidic device. Lab Chip. Jan. 7, 2009;9(1):44-9. doi: 10.1039/b809670h. Epub Oct. 28, 2008.
Schürch et al., "Potential of plant cells in culture for cosmetic applications." Phytochem. Rev. 2008;7:599.
Shah, "Fabrication of monodisperse thermosensitive microgels and gel capsules in microfluidic devices," Soft Matter, 4:2303-2309 (2008).
Sheu et al., Phase separation in polystyrene latex interpenetrating polymer networks. J. Poly. Sci. A. Poly. Chem. 1990;28:629-51. Month not cited on publication.
Shintaku et al. (Microsystem technologies 13.8-10 (2007): 951-958; published online Dec. 1, 2006 (Year: 2006).
Shum et al., Double emulsion templated monodisperse phospholipid vesicles. Langmuir. Aug. 5, 2008;24(15):7651-3. Epub Jul. 10, 2008.
Shum et al., Microfluidic fabrication of monodisperse biocompatible and biodegradable polymersomes with controlled permeability. J Am Chem Soc. Jul. 23, 2008;130(29):9543-9. Epub Jun. 25, 2008.
Simeonov et al., Single nucleotide polymorphism genotyping using short, fluorescently labeled locked nucleic acid (LNA) probes and fluorescence polarization detection. Nucleic Acids Res. Sep. 1, 2002;30(17):e91.
Skjeltorp et al., Preparation of nonspherical, monodisperse polymer particles and their self-organization. J. Colloid Interf. Sci. Oct. 1986;113:577-82.
Sorokin et al., Discrimination between perfect and mismatched duplexes with oligonucleotide gel microchips: role of thermodynamic and kinetic effects during hybridization. J Biomol Struct Dyn. Jun. 2005;22(6):725-34.
Su et al., Microfluidics-Based Biochips: Technology Issues, Implementation Platforms, and Design-Automation Challenges. IEEE Transactions on Computer-Aided Design of Integrated Circuits and Systems. 2006;25(2):211-23. (Feb. 2006).
Sun, Liquid Phase Chip Technology Research Progress. Chinese Journal Experimental Surgery. May 2005;22(5):639-40.
Tan et al., "Monodisperse Alginate Hydrogel Microbeads for Cell Encapsulation" Adv. Mater. 2007;19:2696.
Tawfik, et al. Man-made cell-like compartments for molecular evolution. Nat Biotechnol. Jul. 1998;16(7):652-6.
Ulrich, Chapter 1. General Introduction. Chem. Tech. Carbodiimides. 2007:1-7. Month not cited on publication.
Van Blaaderen, Colloidal molecules and beyond. Science. Jul. 25, 2003;301:470-71.
Van Blaaderen, Colloids get complex. Nature. Feb. 2006;439:545-46.
Van De Hulst et al., Glare points. Appl Opt. Nov. 20, 1991;30(33):4755-63.
Velev et al., Assembly of latex particles by using emulsion droplets. 3. Reverse (water in oil) system. Langmuir. 1997;13:1856-59. Month not cited on publication.

(56) References Cited

OTHER PUBLICATIONS

Velev et al., Assembly of latex particles using emulsion droplets as templates. 1. Microstructured hollow spheres. Langmuir. 1996;12:2374-84. Month not cited on publication.
Velev et al., Assembly of latex particles using emulsion droplets as templates. 2. Ball-like and composite aggregates. Langmuir. 1996;12:2385-91. Month not cited on publication.
Wang et al., Single nucleotide polymorphism discrimination assisted by improved base stacking hybridization using oligonucleotide microarrays. Biotechniques. 2003;35:300-08.
Weaver, "Rapid clonal growth measurements at the single-cell level: gel microdroplets and flow cytometry," Biotechnology, 9:873-877 (1991).
Weitz, Nonspherical engineering of polymer colloids. Web Page. Exp. Soft Condensed Matter Group. Last updated Nov. 10, 2005. 1 page.
Weitz, Packing in the spheres. Science. Feb. 13, 2004;303:968-969.
Whitesides, "Soft lithography in biology and biochemistry," Annual Review of Biomedical Engineering, 3:335-373 (2001).
Xia, "Soft lithography," Annual Review of Material Science, 28:153-184 (1998).
Yin et al., Template-assisted self-assembly: a practical route to complex aggregates of monodispersed colloids with well-defined sizes, shapes, and structures. JACS. 2001;123:8718-29. Published on web Aug. 15, 2001.
Zhang et al., "Exploring Microfluidic Routes to Microgels of Biological Polymers." Macromol. Rapid. Commun. vol. 280, Issue 5, p. 327 (2007).
Zhang et al., "Microfluidic Production of Biopolymer Microcapsules with Controlled Morphology." JACS. 2006;128:12205.
Zhang, "Combinatorial marking of cells and organelles with reconstituted fluorescent proteins," Cell, 119:137-144 (Oct. 1, 2004).
Zhao, J. et al., "Preparation of hemoglobin-loaded nano-sized particles with porous structure as oxygen carriers," Biomaterials, vol. 28, pp. 1414-1422 (2007).
Zimmerman, "Microscale production of hybridomas by hypo-osmolar electrofusion," Hum. Antibody Hybridomas, 3 (Jan. 1992).
Extended European Search Report for Application No. EP 16856059.7 dated Apr. 1, 2019.
International Search Report and Written Opinion for Application No. PCT/US2018/047053 dated Oct. 23, 2018.
European Office Action for Application No. EP 14860623.9 dated Nov. 12, 2019.
International Preliminary Report on Patentability for Application No. PCT/US2018/047053 dated Mar. 5, 2020.
Chinese Office Action dated May 8, 2020 for Application No. CN 201680068910.0.
Japanese Office Action dated Oct. 28, 2020 for Application No. JP 2018-519002.
U.S. Appl. No. 16/779,501, filed Jan. 31, 2020, Weitz et al.
U.S. Appl. No. 14/812,951, filed Jul. 29, 2015, Weitz et al.
U.S. Appl. No. 16/640,598, filed Feb. 20, 2020, Weitz et al.
CN 201680068910.0, May 8, 2020, Chinese Office Action.
JP 2018-519002, Oct. 28, 2020, Japanese Office Action.

\* cited by examiner

SYSTEMS AND METHODS FOR MAKING AND USING GEL MICROSPHERES

RELATED APPLICATIONS

This application is a national stage filing under 35 U.S.C. 371 of Int. Patent Application Serial No. PCT/US2016/056509, filed Oct. 12, 2016, entitled "Systems and Methods for Making and Using Gel Microspheres," which claims the benefit of U.S. Provisional Patent Application Ser. No. 62/241,079, filed Oct. 13, 2015, entitled "Systems and Methods for Making and Using Gel Microspheres," by Weitz, et al., incorporated herein by reference in its entirety.

GOVERNMENT FUNDING

This invention was made with government support under Grant No. NMR-1310266 awarded by the National Science Foundation. The government has certain rights in the invention.

FIELD

The present invention generally relates to microfluidic droplets and, in particular, to multiple emulsion microfluidic droplets.

BACKGROUND

Double emulsions are drops containing at least one smaller drop that is composed of a second, substantially immiscible fluid. These core-shell structured fluids can be used, for instance, as templates to produce capsules; the outer drop contains the material that ultimately forms the shell of the capsule, whereas the inner drop constitutes the capsule interior core. These capsules can be used as vehicles for delivery of active ingredients in many fields, such as food, pharmaceuticals, or cosmetics. However, successful application of these capsules may require good control over their permeability and mechanical stability, parameters that can be tuned with the composition and thickness of the capsule shell. This may involve control over the dimensions and composition of the double emulsions. This control is often difficult to achieve if double emulsions are produced by mechanical stirring or membrane emulsification, since these conventional approaches typically yield double emulsion drops of different sizes that often contain multiple inner droplets.

SUMMARY

The present invention generally relates to microfluidic droplets and, in particular, to multiple emulsion microfluidic droplets. The subject matter of the present invention involves, in some cases, interrelated products, alternative solutions to a particular problem, and/or a plurality of different uses of one or more systems and/or articles.

In one aspect, the present invention is generally directed to a method. In one set of embodiments, the method includes providing droplets of a first fluid comprising polymer, surrounded by a second fluid, contained in a carrier fluid; solidifying the second fluid; causing the polymer in the first fluid to form a gel; and removing the solidified second fluid, which may form a suspension of the gel in the carrier fluid.

In another set of embodiments, the method includes acts of providing droplets comprising solvent and polymer contained in a carrier fluid, causing the polymer to form a gel, and removing the solvent from the gel, which may form a suspension of the gel in the carrier fluid.

In another aspect, the present invention encompasses methods of making one or more of the embodiments described herein, for example, gel microspheres. In still another aspect, the present invention encompasses methods of using one or more of the embodiments described herein, for example, gel microspheres.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

The present invention generally relates to microfluidic droplets and, in particular, to multiple emulsion microfluidic droplets. In certain aspects, particles such as gel particles can be prepared in an aqueous carrier from aqueous droplets (or a non-aqueous carrier from non-aqueous droplets). For example, in some embodiments, double-emulsion droplets of a first fluid, surrounded by a second fluid, contained in a carrier fluid may be prepared, where the first fluid forms a gel and the second fluid is removed. For instance, the second fluid may be dissolved in the carrier fluid, or the second fluid may be hardened, then removed, for example, due to a change in pH. Other embodiments of the present invention are generally directed to kits containing such microfluidic droplets, microfluidic devices for making such microfluidic droplets, or the like.

Certain aspects of the invention are generally directed to systems and methods for making particles, such as gel particles, in an aqueous carrier. Although gel particles can be made from emulsions, e.g., where an aqueous droplet contained within a substantially immiscible oil carrier is then polymerized or gelled to form a particle, such gel particles have not typically been made within aqueous carriers.

Figure 1A:
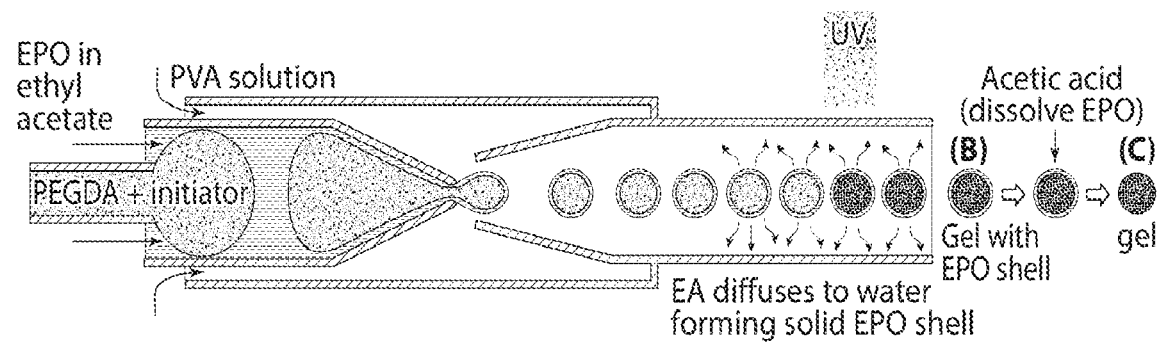
FIGS. 1A-1E illustrate a method for producing gel droplets, in one embodiment of the invention.
Figure 1B:
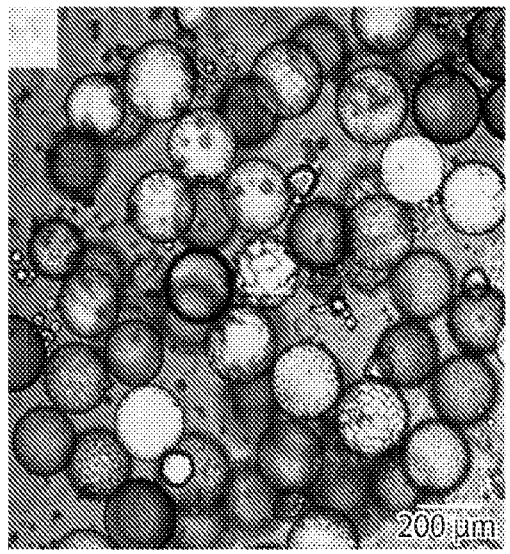
Figure 1C:
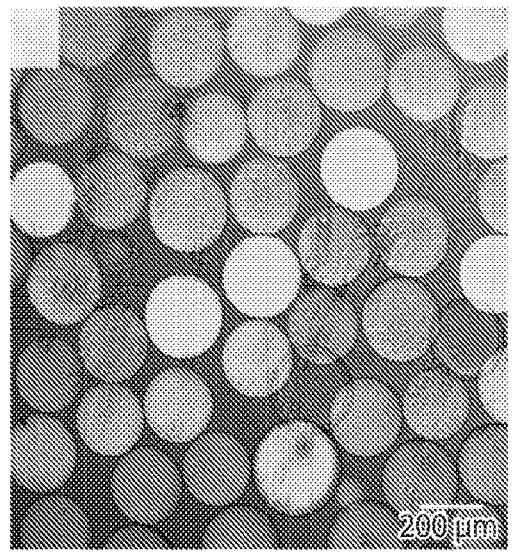

Thus, in one aspect of the invention, particles such as gel particles can be prepared in an aqueous carrier from aqueous droplets. In one set of embodiments, a double emulsion droplet may be prepared. For example, in FIG. 1C, a double emulsion droplet is prepared using a plurality of microfluidic channels, which may be concentrically positioned to produce double emulsion droplets, as is known to those of ordinary skill in the art. It should be understood, however, that FIG. 1C is merely one non-limiting illustrative example of a technique to produce double emulsion droplets; a variety of other techniques to produce a double emulsion droplet could also be used. See, e.g., U.S. Pat. No. 7,776,927 or 9,039,273; Int. Pat. Apl. Pub. Nos. WO 2006/096571, WO 2008/121342, WO 2010/104604, WO 2011/028760, WO 2011/028764, or WO 2012/162296; U.S. Pat. Apl. Pub. Nos. 2009/0012187, 2009/0131543, 2012/0199226, 2012/0211084, or 2013/0046030; Int. Pat. Apl. Ser. No. PCT/US15/25921; or U.S. Pat. Apl. Ser. Nos. 61/980,541 or 62/083,721, each of which is incorporated herein by reference.

In one set of embodiments, a double emulsion droplet may be prepared that comprises an inner (or first) fluid, surround by an outer (or second) fluid, contained in a carrier (or third) fluid. In some cases, the outer fluid may be substantially immiscible with the inner fluid and the carrier fluid, e.g., at least on the time scale of forming double emulsion droplets. The inner fluid may be caused to form a gel, while the second fluid may be hardened, e.g., to form around the inner fluid. These may be performed in any order, e.g., simultaneously or sequentially. After the gel has been formed, the hardened second fluid may then be removed in some fashion, thereby leaving behind a gel in the carrier fluid.

For example, in one set of embodiments, after the double emulsion droplet has been prepared, a polymer within the inner fluid may be polymerized or gelled, for example, by applying ultraviolet light or a change in temperature. For example, the inner fluid may contain agarose gel (which may be solidified, for example, with a change in temperature). For instance, the droplet may be formed at an elevated temperature (e.g., above room temperature, about 25° C.), then cooled (e.g., to room temperature or to a temperature below room temperature); or the droplet may be formed at room temperature, then cooled to a temperature below room temperature, or the like, to cause polymerization or gelation to occur in the inner fluid.

As another example, the inner fluid may be polymerized or gelled chemically. For example, a chemical reaction or a cross-linking reaction may be induced in the inner fluid to cause polymerization or gelation to occur. In some embodiments, the polymerization is a free-radical polymerization, e.g., which may be initiated by exposing the reactants to heat and/or light, such as ultraviolet (UV) light, and/or an initiator, such as a photoinitiator able to produce free radicals (e.g., via molecular cleavage) upon exposure to light. Examples include, but are not limited to, Irgacure 2559, 2-hydroxy-4-(3-triethoxysilylpropoxy)-diphenylketone, or tetramethylethylenediamine. Examples of such polymers include, but are not limited to polyacrylamide, poly(N-isopropylacrylamide), or poly(ethylene glycol) diacrylate. Other species may be present as well.

The outer fluid may be hardened, for example, by inducing a chemical reaction (e.g., between the outer fluid and the carrier fluid), causing precipitation to occur (e.g., if a solvent in the outer fluid then enters the surrounding carrier fluid, leaving behind a polymer that solidifies), changes in temperature, or the like. For example, in one set of embodiments, a first reactant within the fluidic droplet may be reacted with a second reactant within the liquid surrounding the fluidic droplet to produce a solid, which may thus coat the fluidic droplet within a solid "shell" in some cases. A non-limiting example of a solidification reaction is a polymerization reaction involving production of a nylon (e.g., a polyamide), for example, from a diacyl chloride and a diamine. Other examples include polystyrene, polycaprolactone, polyisoprene, poly(lactic acid), polystyrene (PS), polycaprolactone (PCL), polyisoprene (PIP), poly(lactic acid), polyethylene, polypropylene, polyacrylonitrile, polyimide, polyamide, and/or mixtures and/or co-polymers of these and/or other polymers.

As another example, the outer fluid may contain a methacrylate (which may be in polymerized form, i.e., as a polymethacrylate) contained in ethyl acetate, where the ethyl acetate is soluble in water (e.g., in the carrier and/or inner fluids) and can be removed to leave behind the methacrylate (or polymethyacrylate), which can solidify. Non-limiting examples of methacrylates include dimethylaminoethyl methacrylate, butyl methacrylate, ethyl methacrylate, methyl methacrylate, hydroxyethyl methacrylate, trimethylolpropane triacrylate, or the like (including the polymeric forms of these). As yet another example, the outer fluid may contain agarose gel, and the temperature may be lowered (e.g., as discussed above) to cause the agarose gel to solidify to form a "shell" around the inner droplet.

It should be understood that these may happen in any order. For example, the inner fluid may be gelled before or after the outer fluid forms a shell, or both may occur simultaneously.

After the outer fluid hardens into a shell and the inner fluid forms a gel, the outer shell may be removed, for example, mechanically, exposure to a suitable solvent, or other conditional changes (e.g., a change in pH). For example, if the outer shell comprises a polymer, the polymer may be degradable hydrolytically, enzymatically, photolytically, mechanically, etc. As another example, the polymer may be liquefied by heating the polymer above its melting temperature. For example, the outer shell may comprise agarose gel. In yet another example, a methacrylate may be removed upon a change in pH, e.g., to acidic conditions (e.g., a pH of less than 7, less than 6, less than 5, less than 4, less than 3, etc.), thereby leaving behind the gel contained within the carrier fluid. The pH may be changed, for example, by applying a suitable acid or base. The pH may be changed, e.g., by at least about 2, 3, 4, or more pH units. Non-limiting examples of suitable acids include acetic acid, HCl, $H_2SO_4$, $HNO_3$, etc. at any suitable dilution or concentration. Non-limiting examples of suitable bases include NaOH or KOH.

Accordingly, by removing the solidified second fluid, a suspension of gel particles contained in a carrier fluid may be obtained. As noted above, in one set of embodiments, the inner fluid forming the gel particles may be aqueous, yet the carrier fluid may also be aqueous instead of non-aqueous (e.g., an oil). (In addition, in another set of embodiments, both the carrier fluid and the inner fluid may each be non-aqueous as well, while the outer fluid may be aqueous instead.)

It should be understood, however, that the invention is not limited to only double emulsion droplets. In another set of embodiments, particles can be made from single emulsion droplets contained within a carrier fluid, where both the fluid forming the particles and the carrier fluid are aqueous (or alternatively, both may be non-aqueous). For instance, in one aspect, a single-emulsion droplet of a first phase (e.g., an oil phase) may be produced in a carrier phase (e.g., an aqueous or water phase), where the first phase is caused to form a polymer or a gel within the carrier phase. In some cases, the first phase may contain a solvent that is able to enter the surrounding carrier fluid, and/or the solvent may be subsequently removed, e.g., resulting in a polymeric or gel particle contained within the carrier fluid.

The first fluid may be solidified to produce a particle. For example, the first fluid may be fluid polymerized or gelled chemically, e.g., as discussed above. For example, a temperature change, a chemical reaction or a cross-linking reaction may be induced in the first fluid to cause polymerization or gelation to occur. The first fluid may contain any of the materials discussed herein, e.g., agarose, polyacrylamide, poly(N-isopropylacrylamide), or poly(ethylene glycol diacrylate), initiators such as Irgacure 2559, 2-hydroxy-4-(3-triethoxysilylpropoxy)-diphenylketone, or tetramethylethylenediamine, etc.

In some cases, the first fluid may contain a solvent that can be removed, e.g., upon exposure to the surrounding fluid. The solvent may be removed, e.g., sequentially or simultaneously with formation of particles. In some cases, removal of the solvent may cause gelation or polymerization in the first fluid to form particles. In certain embodiments, if the surrounding fluid is an aqueous fluid, the solvent may have relatively low solubility in water, such that initially a separate phase forms (e.g., the first fluid), but the solvent then gradually dissolves in the surrounding fluid. Examples of such solvents include, but are not limited to, dichloromethane, 1,2-dichloroethane, 1-butanol, diethyl ether, ethyl acetate, methyl t-butyl ether (MTBE), or the like.

In some cases, the solvent may have a water solubility of less than about 1 g/ml, less than about 0.5 g/ml, less than about 0.4 g/ml, less than about 0.3 g/ml, less than about 0.2 g/ml, less than about 0.1 g/ml, less than about 0.05 g/ml, less than about 0.04 g/ml, less than about 0.03 g/ml, less than about 0.02 g/ml, less than about 0.01 g/ml, or less than about 0.005 g/ml. In addition, in some embodiments, the solvent may be removed by exposing the solidified particles to a surrounding fluid that can at least partially remove the solvent, e.g., via extraction, dissolution, or other techniques. For example, particles may be collected from the surrounding carrier fluid, which may be replaced by another fluid (e.g., of the same or different composition) to at least partially remove the solvent from the solidified particles.

According to certain aspects, the systems and methods described herein can be used in a plurality of applications. For example, fields in which the particles and multiple emulsions described herein may be useful include, but are not limited to, food, beverage, health and beauty aids, paints and coatings, chemical separations, agricultural applications, and drugs and drug delivery. For instance, a precise quantity of a fluid, drug, pharmaceutical, or other species can be contained in a droplet or particle designed to release its contents under particular conditions. In some instances, cells can be contained within a droplet or particle, and the cells can be stored and/or delivered, e.g., to a target medium, for example, within a subject. Other species that can be contained within a droplet or particle and delivered to a target medium include, for example, biochemical species such as nucleic acids such as siRNA, RNAi, RNA, and DNA, proteins, peptides, or enzymes. Additional species that can be contained within a droplet or particle include, but are not limited to, colloidal particles, magnetic particles, nanoparticles, quantum dots, fragrances, proteins, indicators, dyes, fluorescent species, chemicals, or the like. The target medium may be any suitable medium, for example, water, saline, an aqueous medium, a hydrophobic medium, or the like.

For example, in one set of embodiments, a species may be contained within and/or on the surface of a particle. In some cases, for instance, the species may be bonded (for example, covalently) to the particle, and/or contained (e.g., physically) within the particle. The species may be, for example, DNA or any of other species described above. In some cases, the species may be present within the droplet (e.g., prior to formation of a particle), or added during or after formation of the particle. For example, in one set of embodiments, DNA may be attached to a particle using EDC/NHS coupling (1-ethyl-3-(3-dimethylaminopropyl)carbodiimide/N-hydroxysuccinimide) or other suitable coupling reactions. In other cases, however, DNA (or other species) may be physically contained within the particles.

In one aspect, the present invention is generally directed to a double (or higher) multiple emulsion. Generally, in a double emulsion, a first (or inner) fluidic droplet comprising a first fluid is surrounded by a second (or middle) fluidic droplet comprising a second fluid, which is contained within a continuous, carrier, or third fluid. Typically, a fluid is substantially immiscible with an adjacent fluid, although fluids that are not adjacent need not be immiscible, and may be miscible (or even identical) in some cases. Thus, for example, the first fluid may be immiscible with the second fluid, but may be miscible or immiscible with the third fluid. Similarly, the second fluid may be immiscible with the third fluid. However, it should be understood that immiscibility is not necessarily required in all embodiments; in some cases, two adjacent fluids are not immiscible, but may retain separation in other ways, e.g., kinetically or through short exposure times.

Thus, as a non-limiting example, in a double emulsion droplet, the first fluid (innermost fluid) may be an aqueous or hydrophilic fluid (a "water" phase), the second fluid (middle fluid) may be a lipophilic or hydrophobic or "oil" phase that is substantially immiscible with the aqueous fluid, and the third (or carrier) fluid may be an aqueous fluid (a "water" fluid) that is substantially immiscible with the second fluid. This is sometimes generally referred to as a W/O/W double emulsion droplet (for water/oil/water), although it should be understand that this is mainly for the sake of convenience; for instance, the first fluid can be any suitable aqueous fluid, and it need not be pure water. For example, the aqueous fluid may be water, saline, an aqueous solution, ethanol, or the like, or any other fluid miscible in water. The oil, in contrast, may be immiscible in water, at least when left undisturbed under ambient conditions. In similar fashion, an O/W/O double emulsion droplet may be similarly defined. Furthermore, these principles may be extended to higher-order multiple emulsions droplets. In addition, it should be understood that other arrangements are also possible. For example, in one embodiment, the first fluid, the second fluid, and the third fluid may be all mutually immiscible.

As used herein, two fluids are immiscible, or not miscible, with each other when one is not soluble in the other to a level of at least 10% by weight at the temperature and under the conditions at which the emulsion is produced. For instance, two fluids may be selected to be immiscible within the time frame of the formation of the fluidic droplets. In some embodiments, two fluids (e.g., the carrying fluid and the inner droplet fluid of a multiple emulsion) are compatible, or miscible, while the outer droplet fluid is incompatible or immiscible with one or both of the carrying and inner droplet fluids. In other embodiments, however, all three (or more) fluids may be mutually immiscible, and in certain cases, all of the fluids do not all necessarily have to be water soluble. In still other embodiments, as mentioned, additional fourth, fifth, sixth, etc. fluids may be added to produce increasingly complex droplets within droplets, e.g., a carrying fluid may surround a first fluid, which may in turn surround a second fluid, which may in turn surround a third fluid, which in turn surround a fourth fluid, etc. In addition, the physical properties of each nesting layer of fluidic droplets may each be independently controlled, e.g., by control over the composition of each nesting level.

The droplets may be microfluidic droplets, in some instances. For instance, the outer droplet may have a diameter of less than about 1 mm, less than about 500 micrometers, less than about 200 micrometers, less than about 100 micrometers, less than about 75 micrometers, less than about 50 micrometers, less than about 25 micrometers, less than about 10 micrometers, or less than about 5 micrometers, or between about 50 micrometers and about 1 mm, between about 10 micrometers and about 500 micrometers, or between about 50 micrometers and about 100 micrometers in some cases. However, in some cases, the droplets may be larger. For example, the inner droplet (or a middle droplet) of a triple or other multiple emulsion droplet may have a diameter of less than about 1 mm, less than about 500 micrometers, less than about 200 micrometers, less than about 100 micrometers, less than about 75 micrometers, less than about 50 micrometers, less than about 25 micrometers, less than about 10 micrometers, or less than about 5 micrometers, or between about 50 micrometers and about 1 mm, between about 10 micrometers and about 500 micrometers, or between about 50 micrometers and about 100 micrometers in some cases.

The particles (e.g., gel particles) or droplets described herein may have any suitable average cross-sectional diameter. Those of ordinary skill in the art will be able to determine the average cross-sectional diameter of a single and/or a plurality of particles or droplets, for example, using laser light scattering, microscopic examination, or other known techniques. The average cross-sectional diameter of a single particle or droplet, in a non-spherical particle or droplet, is the diameter of a perfect sphere having the same volume as the non-spherical particle or droplet. The average cross-sectional diameter of a particle or droplet (and/or of a plurality or series of particles or droplets) may be, for example, less than about 1 mm, less than about 500 micrometers, less than about 200 micrometers, less than about 100 micrometers, less than about 75 micrometers, less than about 50 micrometers, less than about 25 micrometers, less than about 10 micrometers, or less than about 5 micrometers, or between about 50 micrometers and about 1 mm, between about 10 micrometers and about 500 micrometers, or between about 50 micrometers and about 100 micrometers in some cases. The average cross-sectional diameter may also be at least about 1 micrometer, at least about 2 micrometers, at least about 3 micrometers, at least about 5 micrometers, at least about 10 micrometers, at least about 15 micrometers, or at least about 20 micrometers in certain cases. In some embodiments, at least about 50%, at least about 75%, at least about 90%, at least about 95%, or at least about 99% of the particles or droplets within a plurality of particles or droplets has an average cross-sectional diameter within any of the ranges outlined in this paragraph.

The plurality of particles (e.g., gel particles) or droplets may have relatively uniform cross-sectional diameters in certain embodiments. The use of particles or droplets with relatively uniform cross-sectional diameters can allow one to control viscosity, the amount of species delivered to a target, and/or other parameters of the delivery of fluid and/or species from the particles or droplets. In some embodiments, the particles or droplets of particles is monodisperse, or the plurality of particles or droplets has an overall average diameter and a distribution of diameters such that no more than about 5%, no more than about 2%, or no more than about 1% of the particles or droplets have a diameter less than about 90% (or less than about 95%, or less than about 99%) and/or greater than about 110% (or greater than about 105%, or greater than about 101%) of the overall average diameter of the plurality of particles or droplets.

In some embodiments, the plurality of particles or droplets has an overall average diameter and a distribution of diameters such that the coefficient of variation of the cross-sectional diameters of the particles or droplets is less than about 10%, less than about 5%, less than about 2%, between about 1% and about 10%, between about 1% and about 5%, or between about 1% and about 2%. The coefficient of variation can be determined by those of ordinary skill in the art, and may be defined as:

$$c_v = \frac{\sigma}{|\mu|}$$

wherein $\sigma$ is the standard deviation and $\mu$ is the mean.

In certain aspects of the present invention, as discussed, multiple emulsions are formed by flowing fluids through one or more channels, e.g., as shown in FIG. 1C. The system may be a microfluidic system. "Microfluidic," as used herein, refers to a device, apparatus, or system including at least one fluid channel having a cross-sectional dimension of less than about 1 millimeter (mm), and in some cases, a ratio of length to largest cross-sectional dimension of at least 3:1. One or more channels of the system may be a capillary tube. In some cases, multiple channels are provided, and in some embodiments, at least some are nested, as described herein. The channels may be in the microfluidic size range and may have, for example, average inner diameters, or portions having an inner diameter, of less than about 1 millimeter, less than about 300 micrometers, less than about 100 micrometers, less than about 30 micrometers, less than about 10 micrometers, less than about 3 micrometers, or less than about 1 micrometer, thereby providing droplets having comparable average diameters. One or more of the channels may (but not necessarily), in cross-section, have a height that is substantially the same as a width at the same point. In cross-section, the channels may be rectangular or substantially non-rectangular, such as circular or elliptical.

As used herein, the term "fluid" generally refers to a substance that tends to flow and to conform to the outline of its container, i.e., a liquid, a gas, a viscoelastic fluid, etc. In one embodiment, the fluid is a liquid. Typically, fluids are materials that are unable to withstand a static shear stress, and when a shear stress is applied, the fluid experiences a continuing and permanent distortion. The fluid may have any suitable viscosity that permits flow. If two or more fluids are present, each fluid may be independently selected among essentially any fluids (liquids, gases, and the like) by those of ordinary skill in the art, by considering the relationship between the fluids.

A variety of materials and methods, according to certain aspects of the invention, can be used to form articles or components such as those described herein, e.g., channels such as microfluidic channels, chambers, etc. For example, various articles or components can be formed from solid materials, in which the channels can be formed via micromachining, film deposition processes such as spin coating and chemical vapor deposition, laser fabrication, photolithographic techniques, etching methods including wet chemical or plasma processes, 3D printing, and the like. See, for example, Scientific American, 248:44-55, 1983 (Angell, et al).

In one set of embodiments, various structures or components of the articles described herein can be formed from glass or a polymer, for example, an elastomeric polymer such as polydimethylsiloxane ("PDMS"), polytetrafluoroethylene ("PTFE" or Teflon®), epoxy, norland optical adhesive, or the like. For instance, according to one embodiment, microfluidic channels may be formed from glass tubes or capillaries. In addition, in some cases, a microfluidic channel may be implemented by fabricating the fluidic system separately using PDMS or other soft lithography techniques (details of soft lithography techniques suitable for this embodiment are discussed in the references entitled "Soft Lithography," by Younan Xia and George M. Whitesides, published in the *Annual Review of Material Science,* 1998, Vol. 28, pages 153-184, and "Soft Lithography in Biology and Biochemistry," by George M. Whitesides, Emanuele Ostuni, Shuichi Takayama, Xingyu Jiang and Donald E. Ingber, published in the *Annual Review of Biomedical Engineering,* 2001, Vol. 3, pages 335-373; each of these references is incorporated herein by reference). In addition, in some embodiments, various structures or components of the articles described herein can be formed of a metal, for example, stainless steel.

Other examples of potentially suitable polymers include, but are not limited to, polyethylene terephthalate (PET), polyacrylate, polymethacrylate, polycarbonate, polystyrene, polyethylene, polypropylene, polyvinylchloride, cyclic olefin copolymer (COC), polytetrafluoroethylene, a fluorinated polymer, a silicone such as polydimethylsiloxane, polyvinylidene chloride, bis-benzocyclobutene ("BCB"), a polyimide, a fluorinated derivative of a polyimide, or the like. Combinations, copolymers, or blends involving polymers including those described above are also envisioned. The device may also be formed from composite materials, for example, a composite of a polymer and a semiconductor material.

In some embodiments, various structures or components of the article are fabricated from polymeric and/or flexible and/or elastomeric materials, and can be conveniently formed of a hardenable fluid, facilitating fabrication via molding (e.g. replica molding, injection molding, cast molding, etc.). The hardenable fluid can be essentially any fluid that can be induced to solidify, or that spontaneously solidifies, into a solid capable of containing and/or transporting fluids contemplated for use in and with the fluidic network. In one embodiment, the hardenable fluid comprises a polymeric liquid or a liquid polymeric precursor (i.e. a "prepolymer"). Suitable polymeric liquids can include, for example, thermoplastic polymers, thermoset polymers, waxes, or mixtures or composites thereof heated above their melting point. As another example, a suitable polymeric liquid may include a solution of one or more polymers in a suitable solvent, which solution forms a solid polymeric material upon removal of the solvent, for example, by evaporation. Such polymeric materials, which can be solidified from, for example, a melt state or by solvent evaporation, are well known to those of ordinary skill in the art. A variety of polymeric materials, many of which are elastomeric, are suitable, and are also suitable for forming molds or mold masters, for embodiments where one or both of the mold masters is composed of an elastomeric material. A non-limiting list of examples of such polymers includes polymers of the general classes of silicone polymers, epoxy polymers, and acrylate polymers. Epoxy polymers are characterized by the presence of a three-membered cyclic ether group commonly referred to as an epoxy group, 1,2-epoxide, or oxirane. For example, diglycidyl ethers of bisphenol A can be used, in addition to compounds based on aromatic amine, triazine, and cycloaliphatic backbones. Another example includes the well-known Novolac polymers. Non-limiting examples of silicone elastomers suitable for use according to the invention include those formed from precursors including the chlorosilanes such as methylchlorosilanes, ethylchlorosilanes, phenylchlorosilanes, dodecyltrichlorosilanes, etc.

Silicone polymers are used in certain embodiments, for example, the silicone elastomer polydimethylsiloxane. Non-limiting examples of PDMS polymers include those sold under the trademark Sylgard by Dow Chemical Co., Midland, Mich., and particularly Sylgard 182, Sylgard 184, and Sylgard 186. Silicone polymers including PDMS have several beneficial properties simplifying fabrication of various structures of the invention. For instance, such materials are inexpensive, readily available, and can be solidified from a prepolymeric liquid via curing with heat. For example, PDMSs are typically curable by exposure of the prepolymeric liquid to temperatures of about, for example, about 65° C. to about 75° C. for exposure times of, for example, about an hour, about 3 hours, about 12 hours, etc. Also, silicone polymers, such as PDMS, can be elastomeric and thus may be useful for forming very small features with relatively high aspect ratios, necessary in certain embodiments of the invention. Flexible (e.g., elastomeric) molds or masters can be advantageous in this regard.

One advantage of forming structures such as microfluidic structures or channels from silicone polymers, such as PDMS, is the ability of such polymers to be oxidized, for example by exposure to an oxygen-containing plasma such as an air plasma, so that the oxidized structures contain, at their surface, chemical groups capable of cross-linking to other oxidized silicone polymer surfaces or to the oxidized surfaces of a variety of other polymeric and non-polymeric materials. Thus, structures can be fabricated and then oxidized and essentially irreversibly sealed to other silicone polymer surfaces, or to the surfaces of other substrates reactive with the oxidized silicone polymer surfaces, without the need for separate adhesives or other sealing means. In most cases, sealing can be completed simply by contacting an oxidized silicone surface to another surface without the need to apply auxiliary pressure to form the seal. That is, the pre-oxidized silicone surface acts as a contact adhesive against suitable mating surfaces. Specifically, in addition to being irreversibly sealable or bonded to itself, oxidized silicone such as oxidized PDMS can also be sealed irreversibly to a range of oxidized materials other than itself including, for example, glass, silicon, silicon oxide, quartz, silicon nitride, polyethylene, polystyrene, glassy carbon, and epoxy polymers, which have been oxidized in a similar fashion to the PDMS surface (for example, via exposure to an oxygen-containing plasma). Oxidation and sealing methods useful in the context of the present invention, as well as overall molding techniques, are described in the art, for example, in an article entitled "Rapid Prototyping of Microfluidic Systems and Polydimethylsiloxane," *Anal. Chem.*, 70:474-480, 1998 (Duffy et al.), incorporated herein by reference.

Different components can be fabricated of different materials. For example, a base portion including a bottom wall and side walls can be fabricated from an opaque material such as silicon or PDMS, and a top portion can be fabricated from a transparent or at least partially transparent material, such as glass or a transparent polymer, for observation and/or control of the fluidic process. Components can be coated so as to expose a desired chemical functionality to fluids that contact interior channel walls, where the base supporting material does not have a precise, desired functionality. For example, components can be fabricated as illustrated, with interior channel walls coated with another material, e.g., as discussed herein. Material used to fabricate various components of the systems and devices of the invention, e.g., materials used to coat interior walls of fluid channels, may desirably be selected from among those materials that will not adversely affect or be affected by fluid flowing through the fluidic system, e.g., material(s) that is chemically inert in the presence of fluids to be used within the device. A non-limiting example of such a coating is disclosed below; additional examples are disclosed in Int. Pat. Apl. Ser. No. PCT/US2009/000850, filed Feb. 11, 2009, entitled "Surfaces, Including Microfluidic Channels, With Controlled Wetting Properties," by Weitz, et al., published as WO 2009/120254 on Oct. 1, 2009, incorporated herein by reference.

In some embodiments, certain microfluidic structures of the invention (or interior, fluid-contacting surfaces) may be formed from certain oxidized silicone polymers. Such surfaces may be more hydrophilic than the surface of an elastomeric polymer. Such hydrophilic surfaces can thus be more easily filled and wetted with aqueous solutions.

In some embodiments, a bottom wall of a microfluidic device of the invention is formed of a material different from one or more side walls or a top wall, or other components. For example, in some embodiments, the interior surface of a bottom wall comprises the surface of a silicon wafer or microchip, or other substrate. Other components may, as described above, be sealed to such alternative substrates. Where it is desired to seal a component comprising a silicone polymer (e.g. PDMS) to a substrate (bottom wall) of different material, the substrate may be selected from the group of materials to which oxidized silicone polymer is able to irreversibly seal (e.g., glass, silicon, silicon oxide, quartz, silicon nitride, polyethylene, polystyrene, epoxy polymers, and glassy carbon surfaces which have been oxidized). Alternatively, other sealing techniques may be used, as would be apparent to those of ordinary skill in the art, including, but not limited to, the use of separate adhesives, bonding, solvent bonding, ultrasonic welding, etc.

Thus, in certain embodiments, the design and/or fabrication of the article may be relatively simple, e.g., by using relatively well-known soft lithography and other techniques such as those described herein. In addition, in some embodiments, rapid and/or customized design of the article is possible, for example, in terms of geometry. In one set of embodiments, the article may be produced to be disposable, for example, in embodiments where the article is used with substances that are radioactive, toxic, poisonous, reactive, biohazardous, etc., and/or where the profile of the substance (e.g., the toxicology profile, the radioactivity profile, etc.) is unknown. Another advantage to forming channels or other structures (or interior, fluid-contacting surfaces) from oxidized silicone polymers is that these surfaces can be much more hydrophilic than the surfaces of typical elastomeric polymers (where a hydrophilic interior surface is desired). Such hydrophilic channel surfaces can thus be more easily filled and wetted with aqueous solutions than can structures comprised of typical, unoxidized elastomeric polymers or other hydrophobic materials.

In one set of embodiments, one or more of the channels within the device may be relatively hydrophobic or relatively hydrophilic, e.g. inherently, and/or by treating one or more of the surfaces or walls of the channel to render them more hydrophobic or hydrophilic. Generally, the fluids that are formed droplets in the device are substantially immiscible, at least on the time scale of forming the droplets, and the fluids will often have different degrees of hydrophobicity or hydrophilicity. Thus, for example, a first fluid may be more hydrophilic (or more hydrophobic) relative to a second fluid, and the first and the second fluids may be substantially immiscible. Thus, the first fluid can from a discrete droplet within the second fluid, e.g., without substantial mixing of the first fluid and the second fluid (although some degree of mixing may nevertheless occur under some conditions). Similarly, the second fluid may be more hydrophilic (or more hydrophobic) relative to a third fluid (which may be the same or different than the first fluid), and the second and third fluids may be substantially immiscible.

Accordingly, in some cases, a surface of a channel may be relatively hydrophobic or hydrophilic, depending on the fluid contained within the channel. In one set of embodiments, a surface of the channel is hydrophobic or hydrophilic relative to other surfaces within the device. In addition, in some embodiments, a relatively hydrophobic surface may exhibit a water contact angle of greater than about 90°, and/or a relatively hydrophilic surface may exhibit a water contact angle of less than about 90°.

In some cases, relatively hydrophobic and/or hydrophilic surfaces may be used to facilitate the flow of fluids within the channel, e.g., to maintain the nesting of multiple fluids within the channel in a particular order. Additional details of such coatings and other systems may be seen in U.S. Provisional Patent Application Ser. No. 61/040,442, filed Mar. 28, 2008, entitled "Surfaces, Including Microfluidic Channels, With Controlled Wetting Properties," by Abate, et al.; and International Patent Application Serial No. PCT/US2009/000850, filed Feb. 11, 2009, entitled "Surfaces, Including Microfluidic Channels, With Controlled Wetting Properties," by Abate, et al., each incorporated herein by reference.

Certain aspects of the invention are generally directed to techniques for scaling up or "numbering up" devices such as those discussed herein. For example, in some cases, relatively large numbers of devices may be used in parallel, for example at least about 10 devices, at least about 30 devices, at least about 50 devices, at least about 75 devices, at least about 100 devices, at least about 200 devices, at least about 300 devices, at least about 500 devices, at least about 750 devices, or at least about 1,000 devices or more may be operated in parallel. In some cases, an array of such devices may be formed by stacking the devices horizontally and/or vertically. The devices may be commonly controlled, or separately controlled, and can be provided with common or separate sources of various fluids, depending on the application.

Those of ordinary skill in the art will be aware of other techniques useful for scaling up or numbering up devices or articles such as those discussed herein. For example, in some embodiments, a fluid distributor can be used to distribute fluid from one or more inputs to a plurality of outputs, e.g., in one more devices. For instance, a plurality of articles may be connected in three dimensions. In some cases, channel dimensions are chosen that allow pressure variations within parallel devices to be substantially reduced. Other examples of suitable techniques include, but are not limited to, those disclosed in International Patent Application No. PCT/US2010/000753, filed Mar. 12, 2010, entitled "Scale-up of Microfluidic Devices," by Romanowsky, et al., published as WO 2010/104597 on Nov. 16, 2010, incorporated herein by reference in its entirety.

The following documents are incorporated herein by reference in their entirety for all purposes: U.S. Provisional Application Ser. No. 61/980,541, filed Apr. 16, 2014, entitled "Systems and methods for producing droplet emulsions with relatively thin shells"; International Patent Publication Number WO 2004/091763, filed Apr. 9, 2004, entitled "Formation and Control of Fluidic Species," by Link et al.; International Patent Publication Number WO 2004/002627, filed Jun. 3, 2003, entitled "Method and Apparatus for Fluid Dispersion," by Stone et al.; International Patent Publication Number WO 2006/096571, filed Mar. 3, 2006, entitled "Method and Apparatus for Forming Multiple Emulsions," by Weitz et al.; International Patent Publication Number WO 2005/021151, filed Aug. 27, 2004, entitled "Electronic Control of Fluidic Species," by Link et al.; International Patent Publication Number WO 2008/121342, filed Mar. 28, 2008, entitled "Emulsions and Techniques for Formation," by Chu et al.; International Patent Publication Number WO 2010/104604, filed Mar. 12, 2010, entitled "Method for the Controlled Creation of Emulsions, Including Multiple Emulsions," by Weitz et al.; International Patent Publication Number WO 2011/028760, filed Sep. 1, 2010, entitled "Multiple Emulsions Created Using Junctions," by Weitz et al.; International Patent Publication Number WO 2011/028764, filed Sep. 1, 2010, entitled "Multiple Emulsions Created Using Jetting and Other Techniques," by Weitz et al.; International Patent Publication Number WO 2009/148598, filed Jun. 4, 2009, entitled "Polymersomes, Phospholipids, and Other Species Associated with Droplets," by Shum, et al.; International Patent Publication Number WO 2011/116154, filed Mar. 16, 2011, entitled "Melt Emulsification," by Shum, et al.; International Patent Publication Number WO 2009/148598, filed Jun. 4, 2009, entitled "Polymersomes, Colloidosomes, Liposomes, and other Species Associated with Fluidic Droplets," by Shum, et al.; International Patent Publication Number WO 2012/162296, filed May 22, 2012, entitled "Control of Emulsions, Including Multiple Emulsions," by Rotem, et al.; International Patent Publication Number WO 2013/006661, filed Jul. 5, 2012, entitled "Multiple Emulsions and Techniques for the Formation of Multiple Emulsions," by Kim, et al.; and International Patent Publication Number WO 2013/032709, filed Aug. 15, 2012, entitled "Systems and Methods for Shell Encapsulation," by Weitz, et al.

In addition, U.S. Provisional Patent Application Ser. No. 62/241,079, filed Oct. 13, 2015, entitled "Systems and Methods for Making and Using Gel Microspheres," by Weitz, et al., is incorporated herein by reference in its entirety.

The following examples are intended to illustrate certain embodiments of the present invention, but do not exemplify the full scope of the invention.

Example 1

This example illustrates a microfluidic approach to fabricate monodisperse hydrogel microspheres using a double emulsion as the template. Polymerizable precursors are added in the inner phase and crosslinked after the generation of double emulsion drops. Depending on the precursor used, different types of middle phase may be used to temporarily separate the inner phase from the outer phase. In one example, the middle phase is a polymer solution in an organic solvent. After the formation of double emulsion drops, the solvent quickly diffuses into water with the polymer precipitating out to form a thin polymeric shell; then the polymer shell is formed by adjusting the pH of the solution. In another example, double emulsion drops are prepared with an oil shell, and then the oil is removed by centrifugation. These methods allow microgels to be obtained conveniently and efficiently. Examples follow with fabrication of poly(ethylene glycol) diacrylate (PEGDA) and polyacrylamide (PAM) microgels.

Poly(ethylene glycol) diacrylate (PEGDA) microgels from double-emulsion templated capsules. To fabricate monodisperse PEGDA microgels, water-in-oil-in-water (W/O/W) double emulsion drops are produced with a very thin oil layer using a glass-capillary based microfluidic device as shown in FIG. 1A. The device has two tapered round capillaries co-axially assembled in a square capillary. Another thin capillary enters into the small-orifice tapered capillary as the inlet of inner phase (FIG. 1A). The middle phase is injected from the gap between the small-orifice tapered capillary and the thin capillary. The outer phase is injected from the gap between the small-orifice tapered capillary and the square capillary. The inner phase first breaks into liquid slugs at the tip of the thin capillary; each liquid slug then breaks into many monodisperse drops with a middle phase shell at the junction of the tapered capillaries. The inner phase was an aqueous solution of 20 wt. % PEGDA (Mw~700, Sigma-Aldrich), 2 wt % PVA (polyvinyl alcohol, Mw~13,000-23,000, 87-89% hydrolyzed, Sigma-Aldrich), 0.2 wt % Irgacure 2959 as the photo-initiator, with a small amount of FITC-dextran (Mw~10 k, Sigma-Aldrich) to facilitate visualization. The middle phase was 10 wt. % Eudragit® EPO dissolved in ethyl acetate; Eudragit® EPO is a cationic copolymer that is soluble in acidic solution up to pH 5. The outer phase was 10 wt. % PVA solution. The pH of the inner and outer phases was adjusted to be 7-7.3 by adding BDH® buffer pH 11.

Figure 1D:
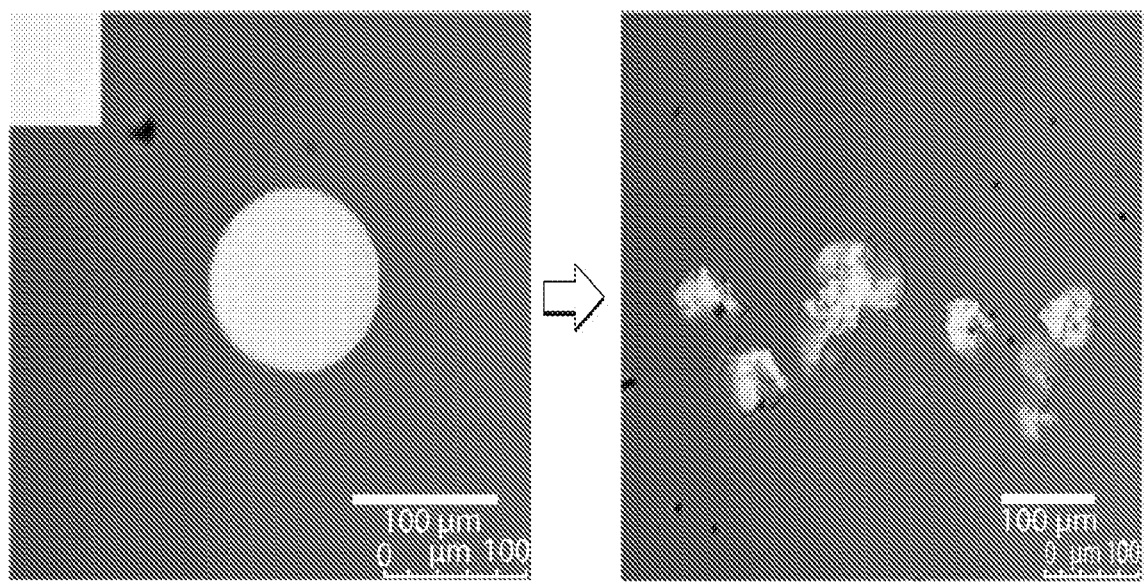

FIG. 1A shows a scheme for microfluidic generation of thin-shell microgel capsules. FIG. 1B shows confocal microscopy images of microgels with pH-responsive polymeric shells. FIG. 1C shows confocal microscopy images of clean microgels after removing the polymeric shells by adding acid. FIG. 1D illustrates that a microgel can be broken into small pieces after being pressed.

Figure 1E:
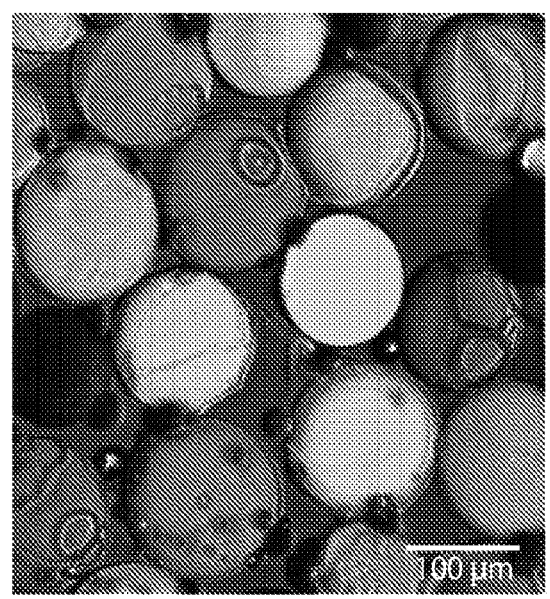

After the double emulsion drops were generated, ethyl acetate quickly diffused into water, with EPO precipitating to form the solid shell. In the meantime, UV light was illuminated on-chip to polymerize the PEGDA in the core. The resultant core-shell capsules were collected in 2 wt % PVA solution of pH 7-7.3. The EPO shell appeared to show wrinkles due to the volume shrinkage of PEGDA during polymerization, as shown in FIG. 1B. Depending on the shell thickness and capsule size, the shell may also crack under some conditions, as shown in FIG. 1E.

To remove the EPO shell, add diluted acetic acid of pH 4 was added to the gel suspension; the EPO was then dissolved by the acidic solution, resulting in PEGDA microgels, as shown in FIG. 1C. When the microgels were pressed between two glass slides, the gel broke into many small pieces without losing the fluorescent dye, indicating that PEGDA was fully polymerized (FIG. 1D).

Example 2

This example illustrates an approach to fabricate polyacrylamide microgels from regular double emulsion. Monodisperse double emulsions were produced using a glass-capillary based microfluidic device as in FIG. 2A. The inner phase was the aqueous solution of 20 wt. % acrylamide, 0.2 wt. % N,N'-Methylenebisacrylamide, and 0.2 wt % Irgacure 2959 with fluorescent microspheres (0.1 micrometers, green). The middle phase was HFE 7500 oil with 1 wt % krytox-PEO surfactant. The outer phase was 10 wt % PVA solution. UV light was applied to the double emulsion drops on-chip before collecting them in a vial. Double emulsion drops and single emulsion HFE drops were generated alternatively in the microfluidic channel in some cases, resulting in a mixture of double emulsion and single emulsion drops, as shown in FIG. 2B.

To remove the HFE oil from the microgels, the sample was centrifuged at a speed of 1000 rpm. After centrifugation, the HFE oil drops settled down at the bottom. The polyacrylamide microgels stayed above the HFE drops, and the top layer was the continuous water phase. The microgels were segregated using a pipette; the resultant microgels are shown in FIG. 2C. When press the microgel were pressed using a glass slide, the gel broke into several small pieces without losing any fluorescence, indicating the complete polymerization of acrylamide.

Figure 2A:
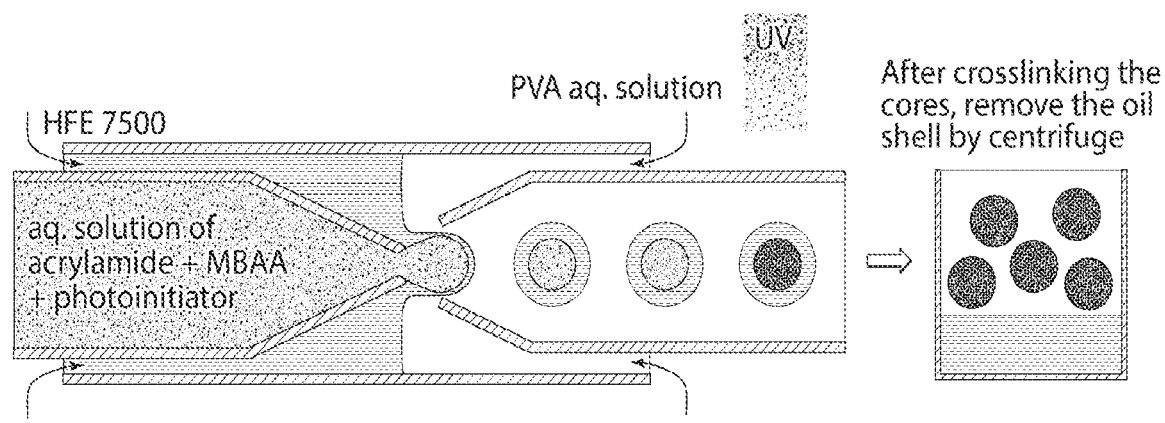
FIGS. 2A-2C illustrate a method for producing gel droplets, in accordance with another embodiment of the invention.
Figure 2B:
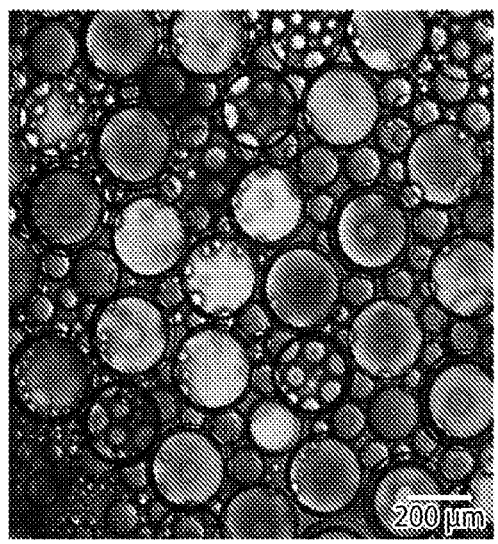
Figure 2C:
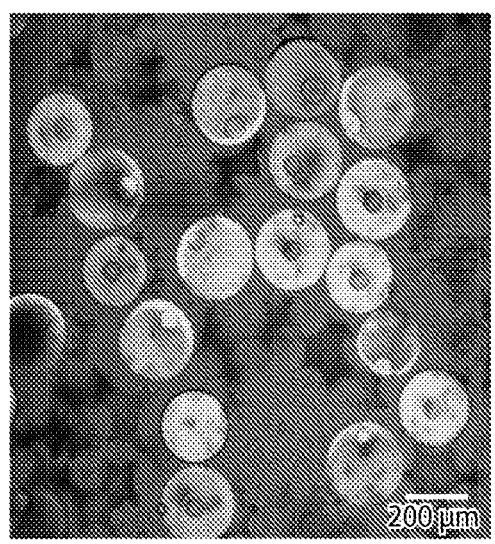

FIG. 2A shows a scheme of microfluidic generation of gel-oil double emulsion. FIG. 2B is a confocal microscopy image of polyacrylamide microgels with an oil shell. FIG. 2C is a confocal microscopy image of clean polyacrylamide microgels after removing the oil shell.

Example 3

Figure 3A:
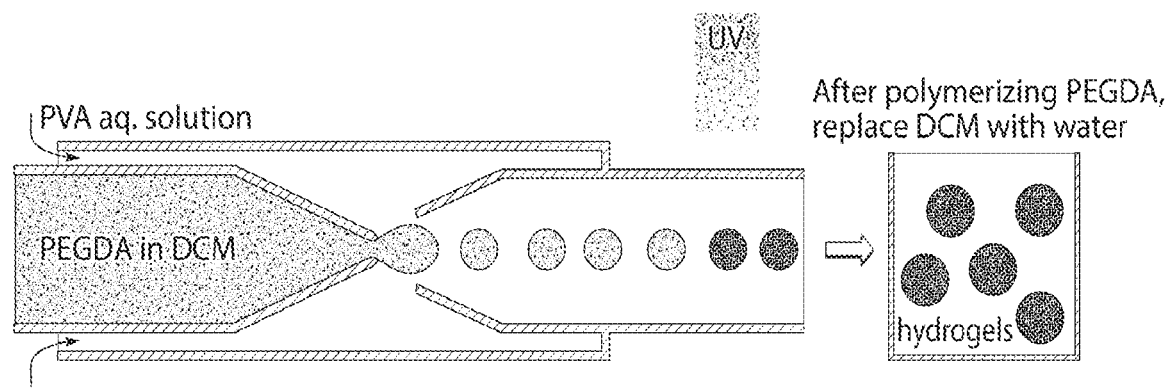
FIGS. 3A-3C illustrate a method for producing gel droplets, in another embodiment of the invention.

This example shows PEGDA hydrogel microspheres prepared from single emulsions. To fabricate a microhydrogel, a glass capillary device was used. Poly(ethylene glycol) diacrylate (PEGDA) with different molecular weight (250, 575, and 700) in dichloromethane (DCM) with volume ratio of 1 to 1 were chosen as inner phase liquid, and 10% PVA aqueous solution was chosen as outer phase liquid. The flow rates for inner and outer phase were 1000 microliters/h and 3500 microliters/h, respectively. Oil-in-water single emulsion droplets were steadily produced, and then UV light was used to crosslink PEGDA in the core to get stable monodisperse spherical drops, as shown in FIG. 3A.

Figure 3B:
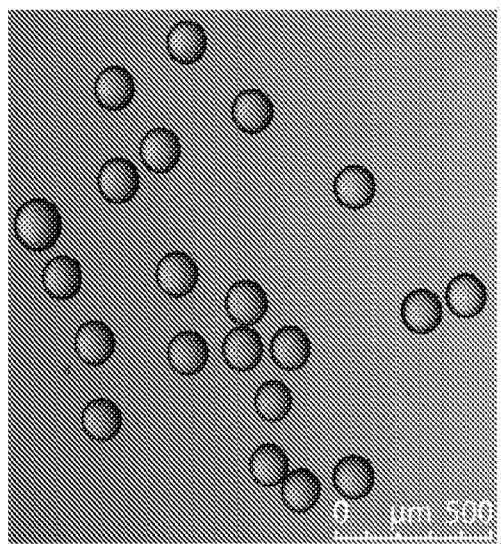
Figure 3C:
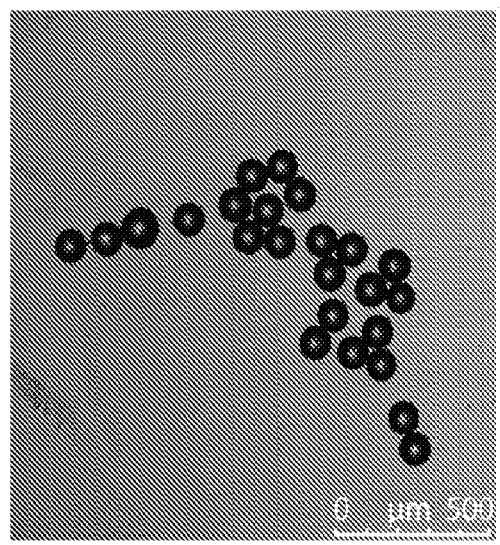

The drops were washed three times with ethanol/water (v/v: 1/1) to remove the inside DCM, and then were immersed into pure water. The supernatant was exchanged with fresh pure water for three times. Finally, PEG microhydrogel drops were suspended in pure deionized water, and were characterized using confocal microscope, as shown in bottom figures. FIG. 3B shows the initial status and FIG. 3C shows the dry status, optical images.

Example 4

This example shows the preparation of poly(ethylene glycol) microhydrogel containing DNA from an O/W single emulsion.

Figure 4:
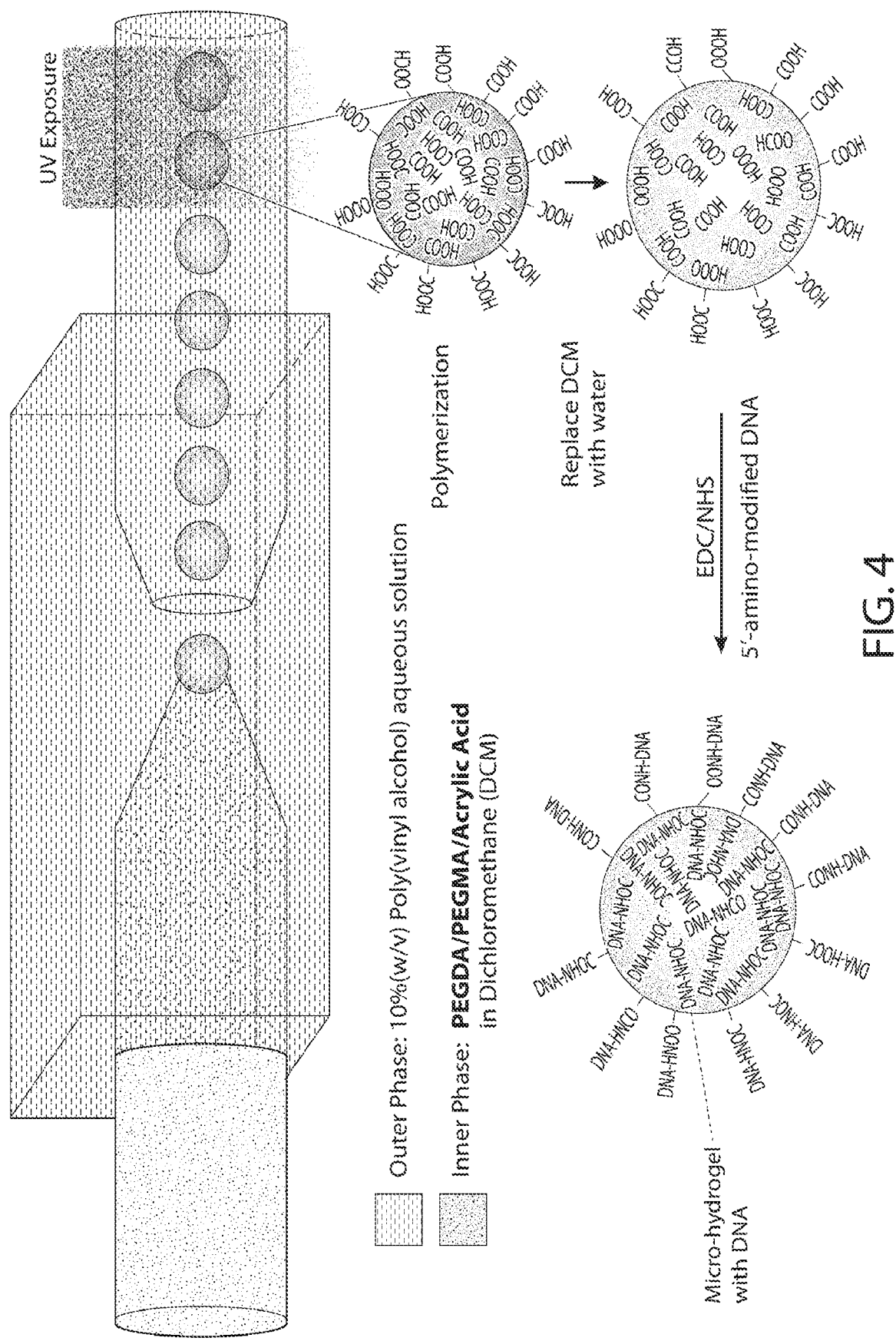
FIG. 4 illustrates a schematic of preparing PEG microhydrogel containing DNA, in another embodiment.

Fabrication of glass capillary microfluidic device. All microhydrogel beads used in this example were prepared using glass capillary microfluidic device. The device was built on a glass slide, with a square glass tube and two cylindrical glass tubes. Briefly, two cylindrical capillaries were pulled with a Flaming/Brown micropipette puller (Model P-97, Sutter Instrument Co., USA) to obtain tapered tips and then their tips were sanded to make a final diameters of 20 and 140 micrometers, respectively. The tapered capillary with small tip was then inserted into a second square capillary and was used as the injection capillary. Another tapered capillary with large tip was inserted into the square capillary at the other side to confine the flow near the injection tip and was used as the collection capillary. Both capillaries were coaxially aligned within the square capillary, as shown in FIG. 4, which shows a schematic illustration of preparing PEG microhydrogel containing DNA.

Preparation of PEG microhydrogel beads. PEG microhydrogel beads were produced from O/W single emulsion droplets using the microfluidic device, followed by UV exposure to polymerize PEG acrylate monomers. The oil phase was made of 20% poly (ethylene glycol) methyl ether acrylate with molecular weight of 480, 5% poly(ethylene glycol) diacrylate with molecular weight of 575 as crosslinker, and 2.5% acrylic acid to bring in carboxyl groups in the hydrogel beads. The solvent was dichloromethane (DCM). 2,2-diethyoxyacetophenone at a concentration of 4% was added to the oil phase as a photoinitiator. The aqueous phase was made of 10% poly(vinyl alcohol) (PVA) in water. Both oil phase and aqueous phase were pumped into the glass capillary device with syringes using Harvard pumps (Harvard Apparatus Hollston, USA). The oil phase was injected into injection capillary with flow rate of 120 microliters/h, and the aqueous phase was injected through an end of square capillary and used as continuous phase with flow rate of 3000 microliters/h. O/W single emulsion drops were formed in the collection capillary. As-formed drops were collected in a glass bottle with 3% PVA solution, followed by UV exposure to produce a crosslinked PEG hydrogel network. As-prepared microhydrogel beads were washed with water and ethanol for several times to remove DCM in the microhydrogel. Finally, the microhydrogel beads were suspended in MES buffer with 1% Tween 20 for further use.

To bind DNA to the PEG microhydrogel, an EDC coupling method was used. 2 mM EDC (1-ethyl-3-(3-dimethylaminopropyl)carbodiimide) and 5 mM NHS (N-hydroxysuccinimide) were added to 1 ml of a microhydrogel bead suspension. After being placed on vortex for 10 min, 50 microliters of 1 mM $NH_2$-DNA were added into the suspension. After reacting for overnight at room temperature, the microhydrogel beads were washed with 1% Tween 20 solution three times; each time took about 30 min. Finally, microhydrogel beads were suspended in buffer solution for further testing.

Figure 5A:
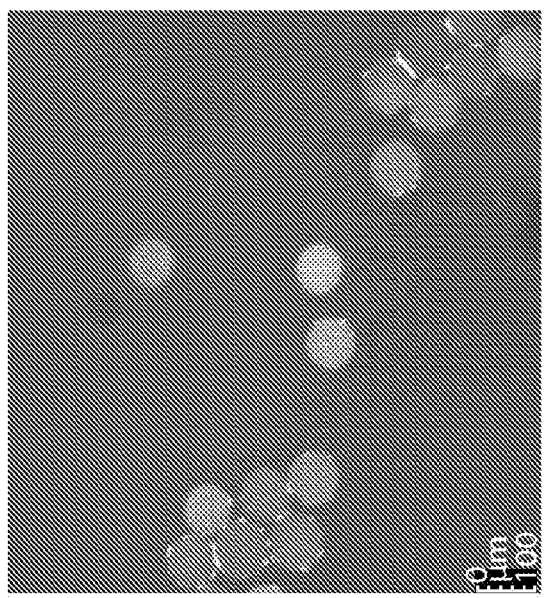
FIGS. 5A-5D show confocal images of PEG microhydrogel with and without DNA, in another embodiment.
Figure 5B:
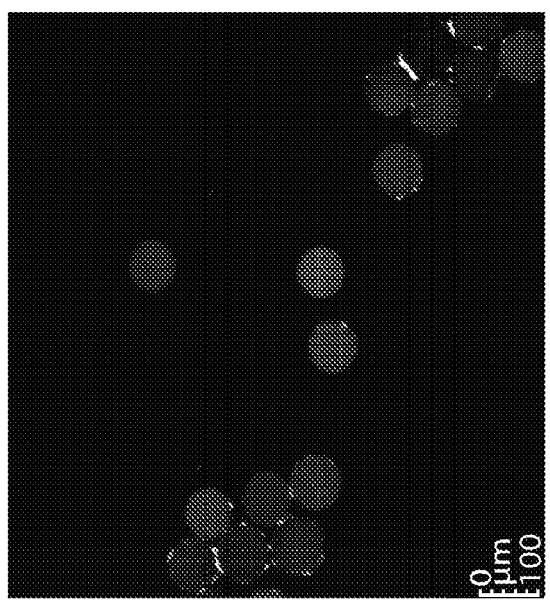
Figure 5C:
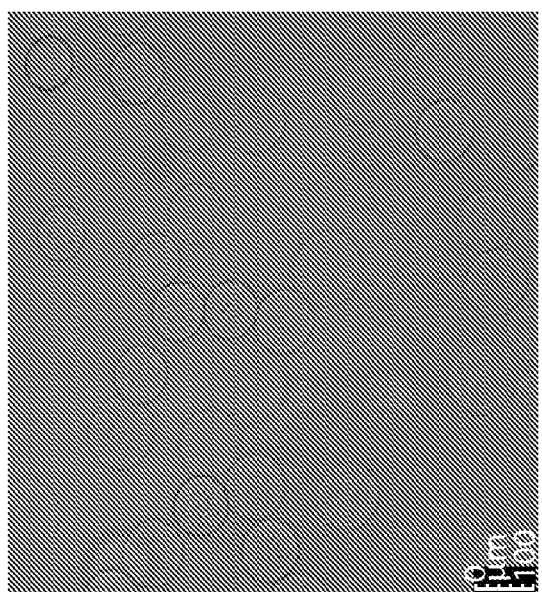
Figure 5D:

To confirm successful incorporation of DNA into microhydrogel, the complementary DNA bearing FAM fluorophore solution was added to the microhydrogel beads suspension. After 45 min, the supernatant solution was removed and the microhydrogel beads were washed with 1% Tween 20 solution three times. Then, confocal fluorescence microscope was used to characterize the PEG microhydrogel with DNA. As a control, as-prepared PEG microhydrogel without DNA functionalization was chosen to be treated with the same process. FIGS. 5A-5B show strong fluorescence signal from PEG microhydrogel functionalized with DNA, while FIGS. 5C-5D show no detectable fluorescent signal for control sample without DNA. These results indicate successful incorporation of DNA with high loading efficiency.

FIGS. 5A and 5B show confocal images of PEG microhydrogel with DNA after be treated with complementary DNA bearing FAM. FIGS. 5C and 5D shows confocal images of PEG microhydrogel without DNA as control after being treated with complementary DNA bearing FAM. FIGS. 5A and 5C are overlapping transmission and fluorescent images; FIGS. 5B and 5D are fluorescent images.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

When the word "about" is used herein in reference to a number, it should be understood that still another embodiment of the invention includes that number not modified by the presence of the word "about."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method, comprising:
providing droplets of a first fluid comprising polymer, surrounded by a second fluid, contained in a carrier fluid within a microfluidic channel;
solidifying the second fluid;
causing the polymer in the first fluid to form a gel; and
removing the solidified second fluid, thereby forming a suspension of the gel in the carrier fluid,
wherein the second fluid comprises a solvent and a second polymer,
wherein solidifying the second fluid comprises causing the solvent to enter the carrier fluid such that the second polymer forms a solid, and
wherein the microfluidic channel comprises a surface exhibiting a water contact angle of greater than about 90°, and/or a relatively hydrophilic surface exhibiting a water contact angle of less than about 90°.

2. The method of claim 1, wherein causing the polymer to form a gel comprises applying ultraviolet light to cross-link the polymer to form the gel.

3. The method of claim 1, wherein causing the polymer to form a gel comprises applying tetramethylethylenediamine (TEMED) to the carrier fluid, whereby the TEMED is able to diffuse into the first fluid.

4. The method of claim 1, wherein solidifying the second fluid comprises solidifying the second fluid by altering the temperature of the second fluid.

5. The method of claim 1, wherein the solidified second fluid is a gel.

6. The method of claim 1, wherein removing the solidified second fluid comprises reducing the pH of the carrier fluid such that the solidified second fluid dissolves in the carrier fluid.

7. The method of claim 1, wherein the first fluid further comprises an initiator.

8. The method of claim 1, wherein the first fluid and the second fluid are immiscible.

9. The method of claim 1, further comprising exposing a species to the gel to incorporate the species into the gel.

10. The method of claim 9, comprising bonding the species to the gel.

11. A method, comprising:
    providing droplets comprising solvent and polymer contained in a carrier fluid within a microfluidic channel;
    causing the polymer to form a gel; and
    removing the solvent from the gel, thereby forming a suspension of the gel in the carrier fluid,
    wherein the solvent is able to form a separate phase when exposed to the carrier fluid, and
    wherein the microfluidic channel comprises a surface exhibiting a water contact angle of greater than about 90°, and/or a relatively hydrophilic surface exhibiting a water contact angle of less than about 90°.

12. The method of claim 11, wherein causing the polymer to form a gel comprises applying ultraviolet light to cross-link the polymer to form the gel.

13. The method of claim 11, wherein causing the polymer to form a gel comprises applying tetramethylethylenediamine (TEMED) to the carrier fluid, whereby the TEMED is able to diffuse into the first fluid.

14. The method of claim 11, wherein the droplets further comprise an initiator.

15. The method of claim 11, wherein removing the solvent from the gel comprises causing the solvent to enter the carrier fluid.

16. The method of claim 11, wherein the carrier fluid is an aqueous fluid.

17. The method of claim 11, further comprising exposing the gel to a species to incorporate the species into the gel.

18. The method of claim 17, comprising bonding the species to the gel.

* * * * *